United States Patent
Braido et al.

(10) Patent No.: US 9,913,715 B2
(45) Date of Patent: Mar. 13, 2018

(54) PARAVALVULAR LEAK SEALING MECHANISM

(71) Applicant: St. Jude Medical, Cardiology Division, Inc., St. Paul, MN (US)

(72) Inventors: Peter N. Braido, Wyoming, MN (US); Mina S. Fahim, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 20 days.

(21) Appl. No.: 15/148,322

(22) Filed: May 6, 2016

(65) Prior Publication Data

US 2016/0250022 A1     Sep. 1, 2016

Related U.S. Application Data

(63) Continuation-in-part of application No. 14/501,200, filed on Sep. 30, 2014, now Pat. No. 9,668,857.
(Continued)

(51) Int. Cl.
    *A61F 2/24*      (2006.01)
(52) U.S. Cl.
    CPC .......... *A61F 2/2418* (2013.01); *A61F 2/2409* (2013.01); *A61F 2210/0061* (2013.01);
(Continued)
(58) Field of Classification Search
    CPC combination set(s) only.
    See application file for complete search history.

(56) References Cited

U.S. PATENT DOCUMENTS 3,409,013 A   11/1968  Berry
3,467,102 A    9/1969  Fogarty et al.
(Continued)

FOREIGN PATENT DOCUMENTS

DE    2246526    3/1973
DE    19532846   3/1997
(Continued)

OTHER PUBLICATIONS

European Search Report for Application No. 14186568.3 dated Mar. 6, 2015.
(Continued)

*Primary Examiner* — Christopher D Prone
(74) *Attorney, Agent, or Firm* — Lerner, David, Littenberg, Krumholz & Mentlik, LLP

(57) ABSTRACT

A collapsible and expandable stent body includes a generally tubular annulus section, one or more prosthetic valve elements mounted to the stent body, and a cuff attached to the stent body. The prosthetic valve is operative to allow flow in an antegrade direction but to substantially block flow in a retrograde direction. The prosthetic heart valve may include paravalvular leak mitigation features in the form of first and second sealing members. The sealing members are attached to the cuff and extend circumferentially around an abluminal surface of the stent body. The sealing members each have an open side facing in a first axial direction and a closed side facing in an opposite second axial direction. Flow of blood in the second axial direction will tend to force blood into the sealing members and cause the sealing members to billow outwardly relative to the stent body, helping to mitigate paravalvular leak.

17 Claims, 8 Drawing Sheets

Related U.S. Application Data

(60) Provisional application No. 61/900,475, filed on Nov. 6, 2013.

(52) U.S. Cl.
CPC ............... *A61F 2220/0075* (2013.01); *A61F 2230/0013* (2013.01); *A61F 2230/0023* (2013.01); *A61F 2230/0026* (2013.01); *A61F 2250/0069* (2013.01)

(56) References Cited

U.S. PATENT DOCUMENTS

| | | |
|---|---|---|
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,983,581 A | 10/1976 | Angell et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,275,469 A | 6/1981 | Gabbay |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,491,986 A | 1/1985 | Gabbay |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goeme et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,258,023 A | 11/1993 | Reger |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,664 A | 5/1995 | Pinchuk |
| 5,443,446 A | 8/1995 | Shturman |
| 5,480,423 A | 1/1996 | Ravenscroft et al. |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,628,786 A | 5/1997 | Banas et al. |
| 5,639,274 A | 6/1997 | Fischell et al. |
| 5,665,115 A | 9/1997 | Cragg |
| 5,693,088 A | 12/1997 | Lazarus |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,769,882 A | 6/1998 | Fogarty et al. |
| 5,776,188 A | 7/1998 | Shepherd et al. |
| 5,800,508 A | 9/1998 | Goicoechea et al. |
| 5,840,081 A | 11/1998 | Andersen et al. |
| 5,843,161 A | 12/1998 | Solovay |
| 5,843,167 A | 12/1998 | Dwyer et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,928,281 A | 7/1999 | Huynh et al. |
| 5,935,163 A | 8/1999 | Gabbay |
| 5,957,949 A | 9/1999 | Leonhardt et al. |
| 5,961,549 A | 10/1999 | Nguyen et al. |
| 6,015,431 A | 1/2000 | Thornton et al. |
| 6,027,525 A | 2/2000 | Suh et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,110,198 A | 8/2000 | Fogarty et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,214,036 B1 | 4/2001 | Letendre et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,264,691 B1 | 7/2001 | Gabbay |
| 6,267,783 B1 | 7/2001 | Letendre et al. |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,312,465 B1 | 11/2001 | Griffin et al. |
| 6,350,277 B1 | 2/2002 | Kocur |
| 6,352,554 B2 | 3/2002 | De Paulis |
| 6,368,348 B1 | 4/2002 | Gabbay |
| 6,419,695 B1 | 7/2002 | Gabbay |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,702 B1 | 12/2002 | Besselink |

(56) References Cited

U.S. PATENT DOCUMENTS

| | | |
|---|---|---|
| 6,488,704 B1 | 12/2002 | Connelly et al. |
| 6,517,576 B2 | 2/2003 | Gabbay |
| 6,533,810 B2 | 3/2003 | Hankh et al. |
| 6,569,196 B1 | 5/2003 | Vesely |
| 6,582,464 B2 | 6/2003 | Gabbay |
| 6,605,112 B1 | 8/2003 | Moll et al. |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,729,356 B1 | 5/2004 | Baker et al. |
| 6,730,118 B2 | 5/2004 | Spenser et al. |
| 6,733,525 B2 | 5/2004 | Yang et al. |
| 6,767,362 B2 | 7/2004 | Schreck |
| 6,780,510 B2 | 8/2004 | Ogle et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,814,754 B2 | 11/2004 | Greenhalgh |
| 6,830,584 B1 | 12/2004 | Seguin |
| 6,837,902 B2 | 1/2005 | Nguyen et al. |
| 6,860,901 B1 | 3/2005 | Baker et al. |
| 6,869,444 B2 | 3/2005 | Gabbay |
| 6,893,460 B2 | 5/2005 | Spenser et al. |
| 6,908,481 B2 | 6/2005 | Cribier |
| 6,911,040 B2 | 6/2005 | Johnson et al. |
| 6,951,573 B1 | 10/2005 | Dilling |
| 7,018,406 B2 | 3/2006 | Seguin et al. |
| 7,025,780 B2 | 4/2006 | Gabbay |
| 7,101,396 B2 | 9/2006 | Artof et al. |
| 7,137,184 B2 | 11/2006 | Schreck |
| 7,147,663 B1 | 12/2006 | Berg et al. |
| 7,160,322 B2 | 1/2007 | Gabbay |
| 7,195,641 B2 | 3/2007 | Palmaz et al. |
| 7,247,167 B2 | 7/2007 | Gabbay |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,571 B2 | 5/2008 | Pease et al. |
| 7,374,573 B2 | 5/2008 | Gabbay |
| 7,381,218 B2 | 6/2008 | Schreck |
| 7,381,219 B2 | 6/2008 | Salahieh et al. |
| 7,393,360 B2 | 7/2008 | Spenser et al. |
| 7,399,315 B2 | 7/2008 | Iobbi |
| 7,452,371 B2 | 11/2008 | Pavcnik et al. |
| 7,462,191 B2 | 12/2008 | Spenser et al. |
| 7,481,838 B2 | 1/2009 | Carpentier et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,597,711 B2 | 10/2009 | Drews et al. |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,871,435 B2 | 1/2011 | Carpentier et al. |
| 7,892,281 B2 | 2/2011 | Seguin et al. |
| 7,914,569 B2 | 3/2011 | Nguyen et al. |
| 7,951,197 B2 | 5/2011 | Lane et al. |
| 7,959,666 B2 | 6/2011 | Salahieh et al. |
| 7,959,672 B2 | 6/2011 | Salahieh et al. |
| 7,959,674 B2 | 6/2011 | Shu et al. |
| 7,967,857 B2 | 6/2011 | Lane |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| 8,083,793 B2 | 12/2011 | Lane et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,226,710 B2 | 7/2012 | Nguyen et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,349,000 B2 | 1/2013 | Schreck |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,685 B2 | 6/2013 | Hariton et al. |
| 8,454,686 B2 | 6/2013 | Alkhatib |
| 8,500,798 B2 | 8/2013 | Rowe et al. |
| 8,512,396 B2 | 8/2013 | Styrc |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,673,000 B2 | 3/2014 | Tabor et al. |
| 8,685,080 B2 | 4/2014 | White |
| 8,728,154 B2 | 5/2014 | Alkhatib |
| 8,747,459 B2 | 6/2014 | Nguyen et al. |
| 8,747,460 B2 | 6/2014 | Tuval et al. |
| 8,764,820 B2 | 7/2014 | Dehdashtian et al. |
| 8,771,345 B2 | 7/2014 | Tuval et al. |
| 8,795,357 B2 | 8/2014 | Yohanan et al. |
| 8,801,776 B2 | 8/2014 | House et al. |
| 8,808,356 B2 | 8/2014 | Braido et al. |

(56) References Cited

U.S. PATENT DOCUMENTS

| | | |
|---|---|---|
| 8,828,078 B2 | 9/2014 | Salahieh et al. |
| 8,834,563 B2 | 9/2014 | Righini |
| 8,840,663 B2 | 9/2014 | Salahieh et al. |
| 8,845,721 B2 | 9/2014 | Braido et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 8,992,608 B2 | 3/2015 | Haug et al. |
| 9,393,110 B2 | 7/2016 | Levi et al. |
| 2001/0021872 A1 | 9/2001 | Bailey et al. |
| 2001/0027338 A1 | 10/2001 | Greenberg |
| 2001/0041928 A1 | 11/2001 | Pavcnik et al. |
| 2002/0032481 A1 | 3/2002 | Gabbay |
| 2002/0036220 A1 | 3/2002 | Gabbay |
| 2002/0173842 A1 | 11/2002 | Buchanan |
| 2003/0023303 A1 | 1/2003 | Palmaz et al. |
| 2003/0040792 A1 | 2/2003 | Gabbay |
| 2003/0050694 A1 | 3/2003 | Yang et al. |
| 2003/0100939 A1 | 5/2003 | Yodfat et al. |
| 2003/0114913 A1 | 6/2003 | Spenser et al. |
| 2003/0130726 A1 | 7/2003 | Thorpe et al. |
| 2003/0212454 A1 | 11/2003 | Scott et al. |
| 2003/0236567 A1 | 12/2003 | Elliot |
| 2003/0236568 A1 | 12/2003 | Hojeibane et al. |
| 2004/0033364 A1 | 2/2004 | Spiridigliozzi et al. |
| 2004/0039436 A1 | 2/2004 | Spenser et al. |
| 2004/0049262 A1 | 3/2004 | Obermiller et al. |
| 2004/0082989 A1 | 4/2004 | Cook et al. |
| 2004/0093075 A1 | 5/2004 | Kuehne |
| 2004/0111111 A1 | 6/2004 | Lin |
| 2004/0186565 A1 | 9/2004 | Schreck |
| 2004/0210304 A1 | 10/2004 | Seguin et al. |
| 2004/0260389 A1 | 12/2004 | Case et al. |
| 2005/0043790 A1 | 2/2005 | Seguin |
| 2005/0075718 A1 | 4/2005 | Nguyen et al. |
| 2005/0075725 A1 | 4/2005 | Rowe |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0234546 A1 | 10/2005 | Nugent et al. |
| 2005/0240200 A1 | 10/2005 | Bergheim |
| 2005/0256566 A1 | 11/2005 | Gabbay |
| 2005/0283231 A1 | 12/2005 | Haug et al. |
| 2006/0004442 A1 | 1/2006 | Spenser et al. |
| 2006/0008497 A1 | 1/2006 | Gabbay |
| 2006/0025855 A1 | 2/2006 | Lashinski et al. |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0122692 A1 | 6/2006 | Gilad et al. |
| 2006/0149350 A1 | 7/2006 | Patel et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0195186 A1 | 8/2006 | Drews et al. |
| 2006/0206202 A1 | 9/2006 | Bonhoeffer et al. |
| 2006/0229719 A1 | 10/2006 | Marquez et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073387 A1 | 3/2007 | Forster et al. |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0239265 A1 | 10/2007 | Birdsall |
| 2007/0244545 A1 | 10/2007 | Birdsall et al. |
| 2007/0244552 A1 | 10/2007 | Salahieh et al. |
| 2007/0270944 A1 | 11/2007 | Bergheim et al. |
| 2007/0288087 A1 | 12/2007 | Fearnot et al. |
| 2008/0021546 A1 | 1/2008 | Patz et al. |
| 2008/0021552 A1 | 1/2008 | Gabbay |
| 2008/0039934 A1 | 2/2008 | Styrc |
| 2008/0071361 A1 | 3/2008 | Tuval et al. |
| 2008/0071369 A1 | 3/2008 | Tuval et al. |
| 2008/0077236 A1 | 3/2008 | Letac et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0208327 A1 | 8/2008 | Rowe |
| 2008/0243245 A1 | 10/2008 | Thambar et al. |
| 2008/0243246 A1 | 10/2008 | Ryan et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0192599 A1 | 7/2009 | Lane et al. |
| 2009/0264997 A1 | 10/2009 | Salahieh et al. |
| 2009/0276027 A1 | 11/2009 | Glynn |
| 2009/0287296 A1 | 11/2009 | Manasse |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0082094 A1 | 4/2010 | Quadri et al. |
| 2010/0087907 A1 | 4/2010 | Lattouf |
| 2010/0100176 A1 | 4/2010 | Elizondo et al. |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0262231 A1 | 10/2010 | Tuval et al. |
| 2010/0286768 A1 | 11/2010 | Alkhatib |
| 2010/0298931 A1 | 11/2010 | Quadri et al. |
| 2011/0022157 A1 | 1/2011 | Essinger et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2011/0282439 A1 | 11/2011 | Thill et al. |
| 2011/0301692 A1 | 12/2011 | Seguin |
| 2011/0319988 A1 | 12/2011 | Schankereli et al. |
| 2012/0035719 A1 | 2/2012 | Forster et al. |
| 2012/0035722 A1 | 2/2012 | Tuval |
| 2012/0046742 A1 | 2/2012 | Tuval et al. |
| 2012/0078347 A1 | 3/2012 | Braido et al. |

(56) References Cited

U.S. PATENT DOCUMENTS

| | | |
|---|---|---|
| 2012/0078357 A1 | 3/2012 | Conklin |
| 2012/0083878 A1 | 4/2012 | Sequin et al. |
| 2012/0101572 A1 | 4/2012 | Kovalsky et al. |
| 2012/0123529 A1 | 5/2012 | Levi et al. |
| 2012/0179244 A1 | 7/2012 | Schankereli et al. |
| 2012/0215303 A1 | 8/2012 | Quadri et al. |
| 2012/0232646 A1 | 9/2012 | Agathos |
| 2012/0277856 A1 | 11/2012 | Spenser et al. |
| 2012/0296418 A1 | 11/2012 | Bonyuet et al. |
| 2012/0303116 A1 | 11/2012 | Gorman, III et al. |
| 2012/0316642 A1 | 12/2012 | Yu et al. |
| 2013/0018458 A1* | 1/2013 | Yohanan ............... A61F 2/2418 623/2.18 |
| 2013/0023984 A1 | 1/2013 | Conklin |
| 2013/0150956 A1 | 6/2013 | Yohanan et al. |
| 2013/0190857 A1 | 7/2013 | Mitra et al. |
| 2013/0204359 A1 | 8/2013 | Thubrikar et al. |
| 2013/0211508 A1 | 8/2013 | Lane et al. |
| 2013/0218267 A1 | 8/2013 | Braido et al. |
| 2013/0274870 A1 | 10/2013 | Lombardi et al. |
| 2013/0274873 A1 | 10/2013 | Delaloye et al. |
| 2013/0338765 A1 | 12/2013 | Braido et al. |
| 2014/0121763 A1 | 5/2014 | Duffy et al. |
| 2014/0142694 A1 | 5/2014 | Tabor et al. |
| 2014/0155997 A1 | 6/2014 | Braido |
| 2014/0194981 A1* | 7/2014 | Menk .................. A61F 2/2418 623/2.17 |
| 2014/0214159 A1 | 7/2014 | Vidlund et al. |
| 2014/0222144 A1* | 8/2014 | Eberhardt ............ A61F 2/2418 623/2.38 |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350663 A1 | 11/2014 | Braido et al. |
| 2014/0350665 A1 | 11/2014 | Braido et al. |
| 2014/0350667 A1 | 11/2014 | Braido et al. |
| 2014/0350668 A1 | 11/2014 | Delaloye et al. |
| 2014/0350669 A1 | 11/2014 | Gillespie et al. |
| 2016/0324633 A1 | 11/2016 | Gross et al. |
| 2017/0020696 A1 | 1/2017 | White |

FOREIGN PATENT DOCUMENTS

| | | |
|---|---|---|
| DE | 19546692 A1 | 6/1997 |
| DE | 19857887 A1 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 4/2002 |
| DE | 10121210 A1 | 11/2002 |
| DE | 102005003632 A1 | 8/2006 |
| DE | 202008009610 U1 | 12/2008 |
| EP | 0103546 | 3/1984 |
| EP | 0144167 | 6/1985 |
| EP | 0592410 | 4/1994 |
| EP | 0850607 A1 | 7/1998 |
| EP | 0597967 B1 | 12/1999 |
| EP | 1000590 A1 | 5/2000 |
| EP | 1057460 A1 | 12/2000 |
| EP | 1088529 | 4/2001 |
| EP | 1360942 A1 | 11/2003 |
| EP | 1570809 A1 | 9/2005 |
| EP | 1584306 A1 | 10/2005 |
| EP | 1598031 A2 | 11/2005 |
| EP | 1926455 A2 | 6/2008 |
| EP | 2047824 A1 | 4/2009 |
| EP | 2059192 B1 | 5/2009 |
| EP | 2254513 A1 | 12/2010 |
| EP | 2537487 A1 | 12/2012 |
| EP | 2620125 A1 | 7/2013 |
| EP | 2749254 A1 | 7/2014 |
| EP | 2815725 A1 | 12/2014 |
| FR | 2788217 A1 | 7/2000 |
| FR | 2847800 A1 | 6/2004 |
| FR | 2850008 A1 | 7/2004 |
| FR | 2847800 B1 | 10/2005 |
| GB | 2056023 | 3/1981 |
| JP | 2008541865 A | 11/2008 |
| JP | 2011500241 A | 1/2011 |
| JP | 2011522634 A | 8/2011 |
| JP | 2011528256 A | 11/2011 |
| JP | 2012504031 A | 2/2012 |
| SU | 158988 | 11/1963 |
| SU | 1271508 | 11/1986 |
| SU | 1371700 | 2/1988 |
| SU | 1457921 A1 | 2/1989 |
| WO | 9117720 A1 | 11/1991 |
| WO | 9217118 | 10/1992 |
| WO | 9301768 B1 | 2/1993 |
| WO | 9716133 A1 | 5/1997 |
| WO | 9724080 A1 | 7/1997 |
| WO | 9832412 A2 | 7/1998 |
| WO | 199829057 A1 | 7/1998 |
| WO | 9913801 A1 | 3/1999 |
| WO | 9933414 | 7/1999 |
| WO | 9940964 | 8/1999 |
| WO | 9947075 | 9/1999 |
| WO | 0018333 A1 | 4/2000 |
| WO | 200041652 A1 | 7/2000 |
| WO | 200047139 A1 | 8/2000 |
| WO | 01/028459 A1 | 4/2001 |
| WO | 0128459 A1 | 4/2001 |
| WO | 0135878 A2 | 5/2001 |
| WO | 0149213 A2 | 7/2001 |
| WO | 200149213 A2 | 7/2001 |
| WO | 0154624 A1 | 8/2001 |
| WO | 0154625 A1 | 8/2001 |
| WO | 0156500 A2 | 8/2001 |
| WO | 01054625 A1 | 8/2001 |
| WO | 01056500 A2 | 8/2001 |
| WO | 200162189 A1 | 8/2001 |
| WO | 2001054625 A1 | 8/2001 |
| WO | 0164137 | 9/2001 |
| WO | 0166035 A2 | 9/2001 |
| WO | 0166037 A2 | 9/2001 |
| WO | 0176510 A2 | 10/2001 |
| WO | 01076510 A2 | 10/2001 |
| WO | 0222054 | 3/2002 |
| WO | 0236048 A1 | 5/2002 |
| WO | 0241789 | 5/2002 |
| WO | 0243620 | 6/2002 |
| WO | 0247575 A2 | 6/2002 |
| WO | 0249540 | 6/2002 |
| WO | 02067782 A2 | 9/2002 |
| WO | 03037222 A2 | 5/2003 |
| WO | 03047468 A1 | 6/2003 |
| WO | 2003047468 A1 | 6/2003 |
| WO | 03075799 A1 | 9/2003 |
| WO | 2004016200 A1 | 2/2004 |
| WO | 2005062980 A2 | 7/2005 |
| WO | 2005070343 A1 | 8/2005 |
| WO | 2005087140 A1 | 9/2005 |
| WO | 2006014233 A2 | 2/2006 |
| WO | 2006034008 A2 | 3/2006 |
| WO | 06073626 A2 | 7/2006 |
| WO | 2006124649 A2 | 11/2006 |
| WO | 2006127765 A1 | 11/2006 |
| WO | 2006128193 A2 | 11/2006 |
| WO | 2007053243 A2 | 5/2007 |
| WO | 07071436 A2 | 6/2007 |
| WO | 2008005405 A2 | 1/2008 |
| WO | 2008035337 A2 | 3/2008 |
| WO | 08070797 A2 | 6/2008 |
| WO | 2008100600 A1 | 8/2008 |
| WO | 2008147964 A1 | 12/2008 |
| WO | 2008150529 A1 | 12/2008 |
| WO | 2009024859 A2 | 2/2009 |
| WO | 2009042196 A2 | 4/2009 |
| WO | 2009045338 A1 | 4/2009 |
| WO | 2009053497 A1 | 4/2009 |
| WO | 2009061389 A2 | 5/2009 |

(56) References Cited

FOREIGN PATENT DOCUMENTS

| WO | 2009149462 A2 | 12/2009 |
|---|---|---|
| WO | 10008549 A1 | 1/2010 |
| WO | 2010008548 A2 | 1/2010 |
| WO | 2010037141 A1 | 4/2010 |
| WO | 10096176 A1 | 8/2010 |
| WO | 10098857 A1 | 9/2010 |
| WO | 2010141847 A1 | 12/2010 |
| WO | 2011057087 A1 | 5/2011 |
| WO | 2012032187 A1 | 3/2012 |
| WO | 2012161786 A1 | 11/2012 |
| WO | 2014110171 A2 | 7/2014 |

OTHER PUBLICATIONS

Percutaneous aortic valve replacement: resection before implantation, 836-840, Quaden, Rene et al., European J. of Cardio-thoracic Surgery, 27 (2005).
Catheter-implanted prosthetic heart valves, Knudsen, L.L., et al., The International Journal of Artificial Organs, vol. 16, No. 5 1993, pp. 253-262.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
"Direct-Access Valve Replacement", Christoph H. Huber, et al., Journal of the American College of Cardiology, vol. 46, vol. 2, (Jul. 19, 2005).
"Percutaneous Aortic Valve Implantation Retrograde From the Femoral Artery", John G. Webb et al., Circulation, 2006; 113:842-850 (Feb. 6, 2006).
"Minimally invasive cardiac surgery", M. J. Mack, Surgical Endoscopy, 2006, 20:S488-S492, DOI: 10.1007/s00464-006-0110-8 (presented Apr. 24, 2006).
"Transapical Transcatheter Aortic Valve Implantation in Humans", Samuel V. Lichtenstein et al., Circulation. 2006; 114: 591-596 (Jul. 31, 2006).
"Transapical approach for sutureless stent-fixed aortic valve implantation: experimental results"; Th. Walther et al., European Journal of Cardio-thoracic Surgery 29 (2006) 703-708 (Jan. 30, 2006).
"Transapical aortic valve implantation: an animal feasibility study"; Todd M. Dewey et al., The annals of thoracic surgery 2006; 82: 110-6 (Feb. 13, 2006).
Textbook "Transcatheter Valve Repair", 2006, pp. 165-186.
Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets In Vitro by Q-Switched 2?μm Microsecond Laser Radiation. Journal of Cardiac Surgery, 30: 157-162. doi: 10.1111/jocs.12481.
Muñoz, Daniel Rodríguez, Carla Lázaro Rivera, and José Luis Zamorano Gómez. "Guidance of treatment of perivalvular prosthetic leaks." Current cardiology reports 16.1 (2014): 1-6.
Gössl, Mario, and Charanjit S. Rihal. "Percutaneous treatment of aortic and mitral valve paravalvular regurgitation." Current cardiology reports 15.8 (2013).
Swiatkiewicz, Iwona, et al. "Percutaneous closure of mitral perivalvular leak." Kardiologia polska 67.7 (2009): 762.
De Cicco, Giuseppe, et al. "Aortic valve periprosthetic leakage: anatomic observations and surgical results." The Annals of thoracic surgery 79.5 (2005): 1480-1485.
Heat Advisor, "Heart repairs without surgery. Minimally invasive procedures aim to correct valve leakage", Sep. 2004, PubMed ID 15586429.

Transcatheter Umbrella Closure of Valvular and Paravalvular Leaks, Houlihan et al., Journal of the American College of Cardiology, vol. 20, No. 6, pp. 1371-1377, (1992).
Buellesfeld et al., Treatment of paravalvular leaks through inverventional techniques; Department of Cardiology, Ben University Hospital 2011.
U.S. Appl. No. 29/375,243, filed Sep. 20, 2010.
U.S. Appl. No. 29/375,260, filed Sep. 20, 2010.
Al Zaibag, Muayed, et al., "Percutaneous Balloon Valvotomy in Tricuspid Stenosis," British Heart Journal, Jan. 1987, vol. 57, No. 1, pp. 51-53.
Al-Khaja N. et al., "Eleven Years' Experience with Carpentier-Edwards Biological Valves in Relation to Survival and Complications," European Journal of Cardiothoracic Surgery 3:305-311, Jun. 30, 2009.
Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.
Andersen, H. R. et al, Transluminal implantation of artificial heart valves, European Heart Journal (1992) 13, 704-708.
Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Andersen, Henning Rud, Transluminal Catheter Implanted Prosthetic Heart Valves, International Journal of Angiology 7:102-106 (1998).
Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.
Bullesfeld et al., Percutaneous Implantation of The First Repositionable Aortic Valve Prosthesis in a Patient With Severe Aortic Stenosis, Catheterization & Cardiovascular Interventions 71:579-84 (2008).
Curriculum Vitae of Robert A. Ersek, M.D., FACS, Jul. 10, 2009, http://www.ersek.com/rae-cv.htm.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
European Communication for Application No. 09788918.2 dated Jun. 29, 2015.
Extended European Search Report for Application No. 14180622.4 dated Nov. 21, 2014.
Extended European Search Report for Application No. 14180623.2 dated Nov. 24, 2014.
Extended European Search Report for Application No. 14180625.7 dated Nov. 24, 2014.
Grube et al., "Percutaneous Implantation of the CoreValve Self-Expanding Valve Prosthesis in High-Risk Patients With Aortic Valve Disease" (2006).
Gössl, Mario, and Charanjit S. Rihal. "Percutaneous treatment of aortic and mitral valve paravalvular regurgitation." Current cardiology reports 15.8 (2013): 1-8.
Hourihan, Maribeth et al., Transcatheter Umbrella Closure of Valvular and Paravalvular Leaks, Hourihan et al., Journal of the American College of Cardiology, vol. 20, No. 6, pp. 1371-1377, (1992).
Inoune, M.D., Kanji, et al., "Clinical Application of Transvenous Mitral Commissurotomy by a New Balloon Catheter," The Journal of Thoracic and Cardiovascular Surgery 87:394-402, 1984.
International Search Report and Written Opinion PCT/US2014/020872 dated Mar. 19, 2014.
International Search Report from corresponding PCT application No. PCT/US2011/054973 dated Apr. 23, 2012.
International Search Report PCT/US2009/004094 dated Mar. 3, 2010.
Knudsen, L.L. et al., Catheter-implanted prosthetic heart valves, The International Journal of Artificial Organs, vol. 16, No. 5 1993, pp. 253-262.

(56) References Cited

OTHER PUBLICATIONS

Kolata, Gina, "Device That Opens Clogged Arteries Gets a Failing Grade in a New Study," nytimes.com, http://www.nytimes.com/1991/01/03/health/device-that-opens-clogged-arteri- es-gets-a-faili . . . , Jul. 29, 2009, 2 pages.
Lawrence, Jr., M.D., David D., "Percutaneous Endovascular Graft: Experimental Evaluation," Radiology 1897; 163: 357-360.
Merriam Webster definition of "retard," www.merriam-webster.com/dictionary/retard, printed Jun. 13, 2016.
Moazami et al., "Transluminal Aortic Valve Placement" (1996).
Moazami et al., "Transluminal Aortic Valve Placement, A Feasibility Study With a Newly Collapsible Aortic Valve," (1996).
Moazami, Nader et al., Transluminal Aortic Valve Placement, ASAIO Journal, 1996; 42:M381-M385.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W., et al., "Der Verschlu.beta. des Ductus Arteriosus Persistens ohne Thorakotomie," Thoraxchirurgie Vaskulare Chirurgie, Band 15, Heft 2, Stuttgart, im Apr. 1967, pp. 199-203, English translation of Abstract only.
Quaden, René et al., "Percutaneous aortic valve replacement: resection before implantation," 836-840, European J. of Cardio-thoracic Surgery 27 (2005).
Rashkind, M.D., William J., "Creationof an Atrial Septal Defect Withoput Thoracotomy," the Journal of the American Medical Association, vol. 196, No. 11, Jun. 13, 1966, pp. 173-174.
Rosch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Ruiz, Carlos, Overview of PRE-CE Mark Transcatheter Aortic Valve Technologies, Euro PCR (powerpoint—dated May 25, 2010).
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, Ulrich, "An Overview of Intravascular Stents: Old and New," Chapter 48, Textbook of Interventional Cardiology, 2nd Edition, W.B. Saunders Company, Philadelphia, PA, .COPYRGT. 1994, 1990, pp. 803-815.
U.S. Appl. No. 13/572,842, filed Aug. 13, 2012, Kovalsky.
Uchida, Barry T., et al., "Modifications of Gianturco Expandable Wire Stents," AJR:150, May 1988, Dec. 3, 1987, pp. 1185-1187.
Urban, M.D., Philip, "Coronary Artery Stenting," Editions Medecine et Hygiene, Geneve, 1991, pp. 5-47.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Wheatley, M.D., David J., "Valve Prostheses," Rob & Smith's Operative Surgery, Fourth Edition, pp. 415-424, Butterworths 1986.
Zegdi, Rachid, MD, PhD et al., "Is It Reasonable to Treat All Calcified Stenotic Aortic Valves With a Valved Stent?" 579-584, J. of the American College of Cardiology, vol. 51, No. 5, Feb. 5, 2008.

* cited by examiner

PARAVALVULAR LEAK SEALING MECHANISM

CROSS-REFERENCE TO RELATED APPLICATIONS

The present application is a continuation-in-part of U.S. patent application Ser. No. 14/501,200, now U.S. Pat. No. 9,668,857, filed Sep. 30, 2014, which claims the benefit of the filing date of U.S. Provisional Patent Application No. 61/900,475 filed Nov. 6, 2013, the disclosures of which are both hereby incorporated by reference herein.

BACKGROUND

The present disclosure relates to heart valve replacement and, in particular, to collapsible prosthetic heart valves. More particularly, the present disclosure relates to collapsible prosthetic heart valves having improved mechanisms to seal against paravalvular leak.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as the sheath covering the valve is withdrawn.

Clinical success of a self-expanding valve may be at least partially dependent on accurate deployment and sealing. For example, inaccurate deployment and anchoring may result in the leakage of blood between the implanted heart valve and the native valve annulus, commonly referred to as perivalvular or paravalvular leakage ("PV leak"). In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage. Additionally, in certain procedures, collapsible valves may be implanted in a native valve annulus without first resecting the native valve leaflets.

BRIEF SUMMARY

One aspect of the present disclosure relates to mechanisms and features for prosthetic valves to facilitate sealing against paravalvular leaks. These mechanisms may include, for example, patches or other types of material that expand or billow open upon PV leak to create a better seal between the prosthetic valve and the native tissue in which the prosthetic valve is implanted.

In one embodiment of the disclosure, a prosthetic heart valve includes a stent body including a generally tubular annulus section defining a first circumferential row of cells. The prosthetic heart valve may include one or more prosthetic valve elements mounted to the stent body and operative to allow flow in an antegrade direction but to substantially block flow in a retrograde direction through the annulus section. The prosthetic heart valve may further include a cuff attached to the stent body and positioned on a luminal surface of the stent body. At least one sealing member may be attached to the cuff, the at least one sealing member having an open side facing in a first axial direction and a closed side facing in a second axial direction opposite to the first axial direction so that a flow of blood in the second axial direction will tend to force blood into the at least one sealing member and cause the sealing member to billow outwardly relative to the stent body. The at least one sealing member may have a shape chosen from the group consisting of generally triangular, generally trapezoidal, and generally semicircular.

In another embodiment of the disclosure, a prosthetic heart valve includes a stent body including a generally tubular annulus section defining a first circumferential row of cells and a second circumferential row of cells distal to the first circumferential row of cells. The prosthetic heart valve may also include one or more prosthetic valve elements mounted to the stent body and operative to allow flow in an antegrade direction but to substantially block flow in a retrograde direction through the annulus section. The prosthetic heart valve my further include a cuff attached to the stent body and positioned on a luminal surface of the stent body. At least one proximal sealing member may be attached to the cuff and positioned substantially within a cell in the first circumferential row of cells, the proximal sealing member having an open side facing in a first axial direction and a closed side facing in a second axial direction opposite the first axial direction so that a flow of blood in the second axial direction will tend to force blood into the proximal sealing member and cause the proximal sealing member to billow outwardly relative to the stent body. At least one distal sealing member may be attached to the cuff and positioned substantially within a cell in the second circumferential row of cells, the distal sealing member having an open side facing in the first axial direction and a closed side facing in the second axial direction so that the flow of blood in the second axial direction will tend to force blood into the distal sealing member and cause the distal sealing member to billow outwardly relative to the stent body.

In yet a further embodiment of the disclosure, a prosthetic heart valve includes a stent body including a generally tubular annulus section and one or more prosthetic valve elements mounted to the stent body and operative to allow flow in an antegrade direction but to substantially block flow in a retrograde direction through the annulus section. A cuff may be attached to the stent body and positioned on a luminal surface of the stent body. A sealing member may be attached to the cuff, the sealing member being generally rectangular and having an open side facing in a first axial direction and a closed side facing in a second axial direction opposite to the first axial direction so that a flow of blood in the second axial direction will tend to force blood into the sealing member and cause the sealing member to billow outwardly relative to the stent body. The sealing member may be wrapped around an entire circumference of the stent body and define a pocket divided into a plurality of regions, each of the regions being in fluid communication with adjacent ones of the regions.

In still a further embodiment of the disclosure, a prosthetic heart valve includes a stent body including a generally tubular annulus section, and one or more prosthetic valve elements mounted to the stent body and operative to allow flow in an antegrade direction but to substantially block flow in a retrograde direction through the annulus section. A cuff may be attached to the stent body and positioned on a luminal surface of the stent body. At least one strut may form a finger at a proximal end thereof. The finger may be configured to lie substantially parallel to the stent body when the stent body is in a collapsed condition and may be configured to curve radially outwardly and distally when the stent body is in an expanded condition, the cuff being attached to the finger.

In a further embodiment of the disclosure, a prosthetic heart valve includes a collapsible and expandable stent body including a generally tubular annulus section and one or more prosthetic valve elements mounted to the stent body and operative to allow flow in an antegrade direction but to substantially block flow in a retrograde direction through the annulus section. A cuff may be attached to the stent body. A first sealing member is attached to the cuff, the first sealing member extending circumferentially around an abluminal surface of the stent body and having an open side facing in a first axial direction and a closed side facing in a second axial direction opposite to the first axial direction so that a flow of blood in the second axial direction will tend to force blood into the first sealing member and cause the first sealing member to billow outwardly relative to the stent body. A second sealing member is attached to the cuff, the second sealing member extending circumferentially around the abluminal surface of the stent body and having an open side facing in the first axial direction and a closed side facing in the second axial direction so that the flow of blood in the second axial direction will tend to force blood into the second sealing member and cause the second sealing member to billow outwardly relative to the stent body. The first sealing member may define a first pocket having a plurality of first regions, each of the first regions being in fluid communication with adjacent ones of the first regions. Similarly, the second sealing member may define a second pocket having a plurality of second regions, each of the second regions being in fluid communication with adjacent ones of the second regions. The first sealing member and/or the second sealing member may be wrapped around an entire circumference of the stent body. The open side of the first sealing member and/or the open side of the second sealing member may be attached to the cuff at spaced locations around a circumference of the stent body. The open side of the first sealing member may include a first plurality of openings and the open side of the second sealing members may include a second plurality of openings, the first plurality of openings being offset in a circumferential direction from the second plurality of openings. The first sealing member may be positioned nearer an inflow end of the stent body than the second sealing member. The open side of the first sealing member may be axially spaced apart from the closed side of the second sealing member. The first sealing member may comprise an extension of the cuff, the extension being wrapped around an inflow end of the stent body such that the extension is positioned on an abluminal surface of the stent body. A proximal portion of the extension on the abluminal surface of the stent body may be connected to a proximal portion of the cuff on the luminal surface of the stent body with a seam. The first sealing member and/or the second sealing member may be formed from a separate piece of material from the cuff. The first sealing member and/or the second sealing member may be formed of a single piece of material or a plurality of pieces of material. The first sealing member and/or the second sealing member may be substantially rectangular.

Various embodiments of the present disclosure will now be described with reference to the appended drawings. It is to be appreciated that these drawings depict only some embodiments of the heart valve according to the descriptions herein and are therefore not to be considered limiting of the scope of the present disclosure.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. The term "circumferential," when used in connection with a prosthetic heart valve, refers to the direction around the perimeter of the valve. Also, when used herein, the words "generally" and "substantially" are intended to mean that slight variations from absolute are included within the scope of the structure or process recited.

Figure 1:
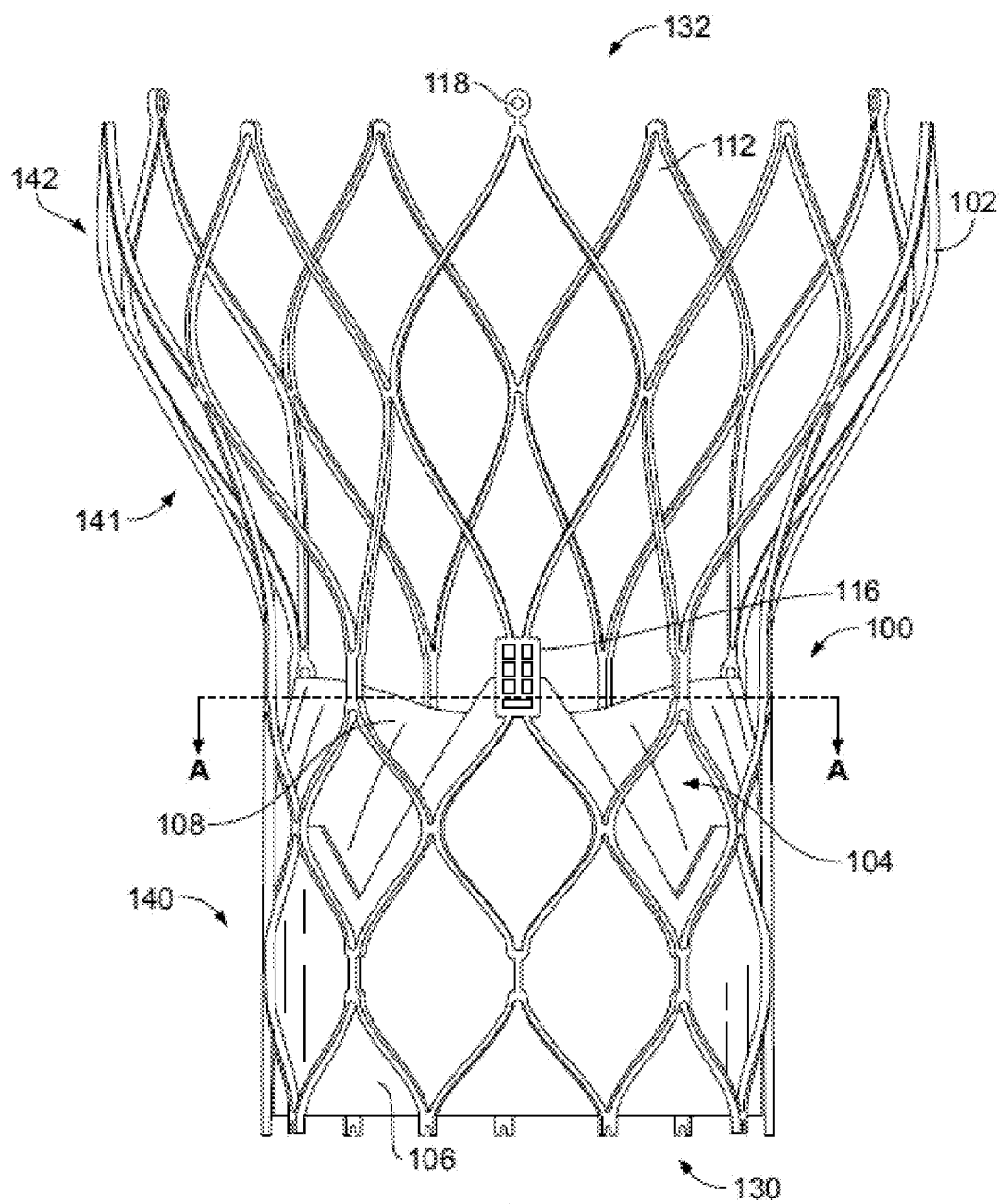
FIG. 1 is a side elevational view of a conventional prosthetic heart valve.

FIG. 1 shows a collapsible stent-supported prosthetic heart valve 100 known in the art. The prosthetic heart valve 100 is designed to replace the function of a native tricuspid, bicuspid or unicuspid valve of a patient, such as a native aortic valve. It should be noted that while the present disclosure is described predominantly in connection with prosthetic aortic valves and a stent having a shape as illustrated in FIG. 1, the concepts described herein may also be used with prosthetic bicuspid valves, such as prosthetic mitral valves, and with stents having different shapes, such as those having a flared or conical annulus section, a less-bulbous aortic section, and the like, and a differently shaped transition section. Examples of collapsible prosthetic heart valves are described in International Patent Application Publication No. WO/2009/042196; U.S. Pat. No. 7,018,406; and U.S. Pat. No. 7,329,278, the disclosures of all of which are hereby incorporated herein by reference.

Prosthetic heart valve 100 will be described in more detail with reference to FIG. 1. Prosthetic heart valve 100 includes expandable stent 102, which may be formed from biocompatible materials that are capable of self-expansion, such as, for example, shape memory alloys such as nitinol. Stent 102 extends from proximal or annulus end 130 to distal or aortic end 132, and includes tubular annulus section 140 adjacent the proximal end and aortic section 142 adjacent the distal end. Annulus section 140 has a relatively small cross-section in the expanded condition, while aortic section 142 has a relatively large cross-section in the expanded condition. Preferably, annulus section 140 is in the form of a cylinder having a substantially round cross-section and a substantially constant diameter along its length. Transition section 141 may taper outwardly from annulus section 140 to aortic section 142. Each of the sections of stent 102 includes a plurality of cells 112 connected to one another in one or more annular rows around the stent. For example, as shown in FIG. 1, annulus section 140 may have two annular rows of cells 112 and aortic section 142 and transition section 141 may each have one or more annular rows of cells. Cells 112 in aortic section 142 may be larger than the cells in annulus section 140. The larger cells in aortic section 142 better enable prosthetic valve 100 to be positioned in the native valve annulus without the stent structure interfering with blood flow to the coronary arteries.

Stent 102 may include one or more retaining elements 118 at distal end 132 thereof, the retaining elements being sized and shaped to cooperate with retaining structures provided on the deployment device (not shown). The engagement of retaining elements 118 with retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed. In some variations, retaining elements 118 may be disposed near proximal end 130 of heart valve 100.

Prosthetic heart valve 100 includes one or more prosthetic valve elements, such as valve assembly 104, preferably positioned in the annulus section 140 of stent 102 and secured to the stent. Valve assembly 104 includes cuff 106 and a plurality of leaflets 108, which collectively function as a one-way valve by coapting with one another, generally allowing blood to flow in an antegrade direction while substantially blocking blood from flowing in a retrograde direction. As a prosthetic aortic valve, valve 100 has three leaflets 108. However, it will be appreciated that other prosthetic heart valves with which the active sealing mechanisms of the present disclosure may be used may have a greater or lesser number of leaflets.

Although cuff 106 is shown in FIG. 1 as being disposed on the luminal or inner surface of annulus section 140, it is contemplated that the cuff may be disposed on the abluminal or outer surface of the annulus section or may cover all or part of either or both of the luminal and abluminal surfaces. Both cuff 106 and leaflets 108 may be wholly or partly formed of any suitable biological material or polymer such as, for example, polytetrafluoroethylene (PTFE), ultra high molecular weight polyethylene (UHMWPE), polyethylene terephthalate (PET), silicone, urethane, and combinations of the preceding materials.

Leaflets 108 may be attached along their belly portions to cells 112 of stent 102, with the commissure between adjacent leaflets attached to commissure attachment features ("CAFs") 116. The particular size and shape of CAFs 116 may vary in different valves, for example valves with larger or smaller diameters may include CAFs that are sized or shaped differently than the illustrated CAFs. As can be seen in FIG. 1, each CAF 116 may lie at the intersection of four cells 112 of stent 102, two of the cells being adjacent one another in the same annular row, and the other two cells being in different annular rows and lying in end-to-end relationship. Preferably, CAFs 116 are positioned entirely within the annulus section 140 of stent 102 or at the juncture of annulus section 140 and transition section 141. CAFs 116 may include one or more eyelets which facilitate the suturing of the leaflet commissure to the stent.

Prosthetic heart valve 100 may be used to replace, for example, a native aortic valve, a surgical heart valve, a repair device or a heart valve that has undergone a surgical procedure. The prosthetic heart valve may be delivered to the desired site (e.g., near the native aortic annulus) using any suitable delivery device. During delivery, the prosthetic heart valve is disposed inside the delivery device in the collapsed condition. The delivery device may be introduced into a patient using a transfemoral, transapical, transseptal, transaortic, subclavian or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When the prosthetic heart valve is properly positioned inside the heart, it works as a one-way valve, allowing blood to flow from the left ventricle of the heart to the aorta, and preventing blood from flowing in the opposite direction. However, as described in greater detail below, some amount of blood may unintentionally flow in the opposite direction around the outside of the prosthetic heart valve due to PV leak.

Figure 2:
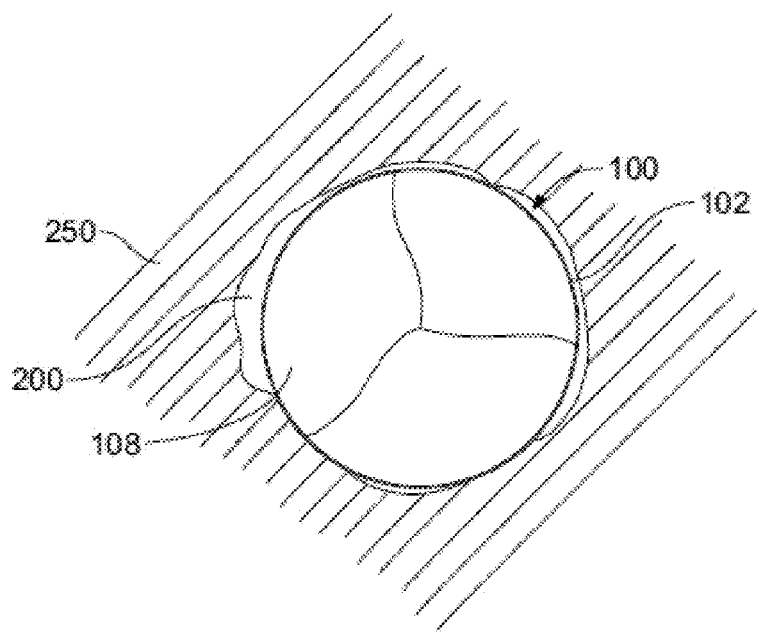
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, annulus section 140 of stent 102 has a substantially circular cross-section which is disposed within non-circular native valve annulus 250. It should be understood that the depiction of native valve annulus 250 in FIG. 2, represented as diagonal lines, is not intended to represent the anatomical shape of the native valve annulus. At certain locations around the perimeter of heart valve 100, crescent-shaped gaps 200 form between the heart valve and native valve annulus 250. Blood flowing through these gaps and past valve assembly 104 of prosthetic heart valve 100 can cause regurgitation and other inefficiencies which reduce cardiac performance. Such improper fitment may be due to bending of stent 102 upon application of force, or due to suboptimal native valve annulus geometry due, for example, to calcification of native valve annulus 250 or to unresected native leaflets. Embodiments of prosthetic heart valves disclosed herein address PV leak that may occur through gaps 200.

Figure 3A:
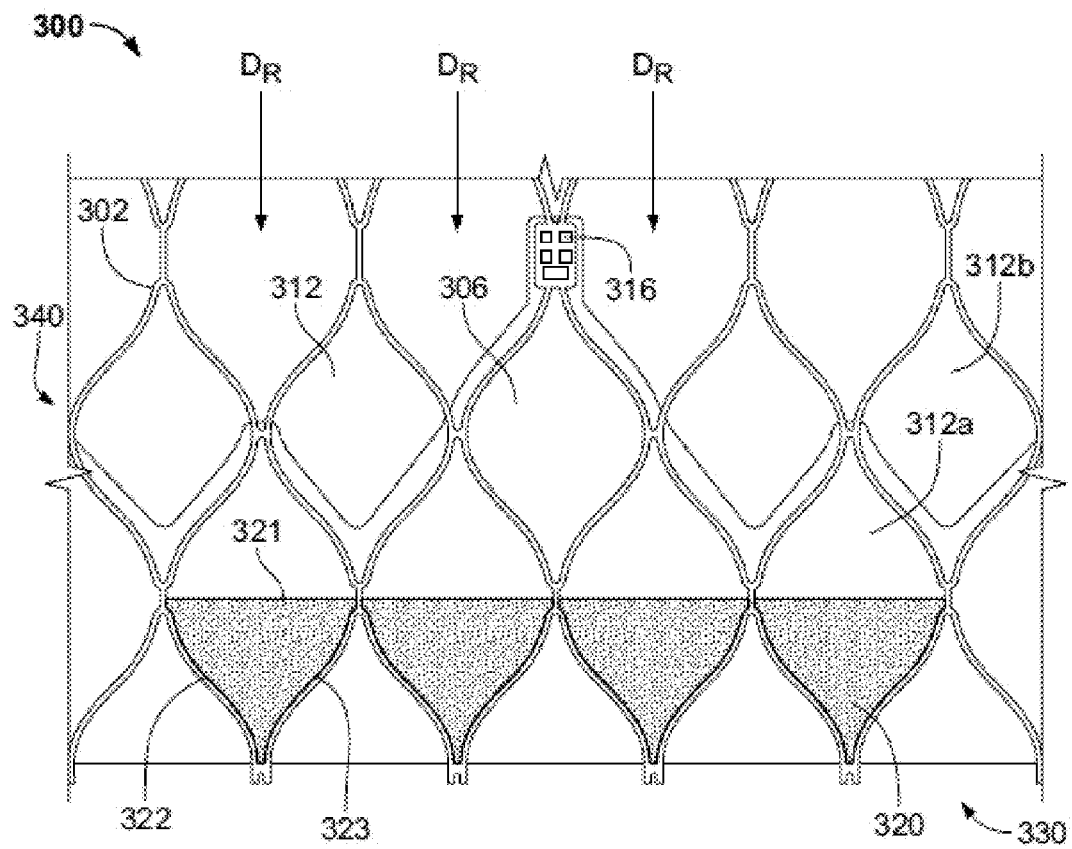
FIG. 3A is an enlarged partial schematic view of a sealing member attached to a stent according to an embodiment of the disclosure.

FIG. 3A illustrates a portion of prosthetic heart valve 300 according to an embodiment of the disclosure. In particular, prosthetic heart valve 300 includes an active sealing mechanism for sealing against PV leak in the form of one or more sealing members 320. In this example, sealing members 320 take the form of parachute-like elements that billow open when blood flows in a retrograde direction $D_R$ into the parachute-like elements. If retrograde flow occurs on the abluminal side of valve 300, the blood may enter one or more sealing members 320, causing the sealing members to billow open and facilitating the sealing of gap spaces between the patient's anatomy and the valve. It should also be noted, for this and other embodiments described herein, sealing members 320 may help seal a gap space between prosthetic valve 300 and the native anatomy, even if there is little or no PV leak to cause the sealing members to billow open. This may be due to, for example, the additional material of sealing members 320 filling gap spaces by virtue of the material being positioned in those gap spaces.

In the illustrated embodiment, prosthetic heart valve 300 includes an expandable stent 302 with a plurality of CAFs 316 (only one illustrated in FIG. 3A), which may be similar in many or all respects to stent 102 and CAFs 116 of FIG. 1. Stent 302 extends from proximal or annulus end 330 to a distal or aortic end (not shown), and includes annulus section 340 adjacent the proximal end and an aortic section (not shown) adjacent the distal end. Each of the sections of stent 302 includes a plurality of cells 312 connected to one another in one or more annular rows around the stent. For example, as shown in FIG. 3A, annulus section 340 may have two annular rows of cells 312, including a first proximalmost circumferential row of cells 312a and a second circumferential row of cells 312b distal to the first row. Valve 300 may also include cuff 306, which may be substantially similar to cuff 106 of FIG. 1. Preferably, cuff 306 has a relatively straight proximal end. In the illustrated embodiment, cuff 306 is positioned on the luminal side of stent 302 and attached to the stent, for example, by sutures (not illustrated).

Sealing members 320 may take the form of generally triangular patches of material, although other shapes may be suitable. The triangular patches may be attached to cuff 306 during valve assembly, or after valve assembly is otherwise complete. Any suitable attachment method, such as sewing, may be used. Preferably, a distal or open side 321 of each sealing member 320, in this case the distal side of the triangular patch, is left partially or completely unconnected to cuff 306. For example, if sewing the triangular patch to cuff 306, two proximal sides 322, 323 of the triangle, meeting at a proximalmost point, are sewn to the cuff, but the open side 321 of the triangle is not. With this configuration, the open side 321 of sealing member 320 remains capable of opening upon retrograde blood flow, with the open side facing the distal end of valve 300. Further, the closed proximal sides 322, 323 that are connected to cuff 306 restrict blood from exiting through the proximal sides of sealing member 320. Proximal sides 322, 323 may be sewn such that open side 321 is loose or floppy, and not taut, thereby enabling blood to flow into sealing member 320. As described above, if retrograde blood flow does occur on the abluminal side of valve 300, the parachuting or billowing action of sealing members 320 upon blood flowing into the sealing members facilitates active sealing between the prosthetic heart valve and the native tissue surrounding the valve.

Figure 3B:
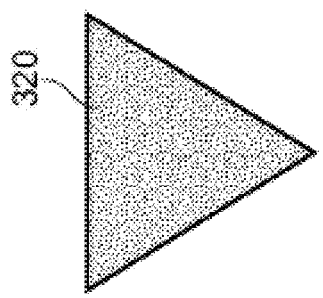
FIG. 3B is a schematic view of an isolated individual sealing member.
Figure 3C:
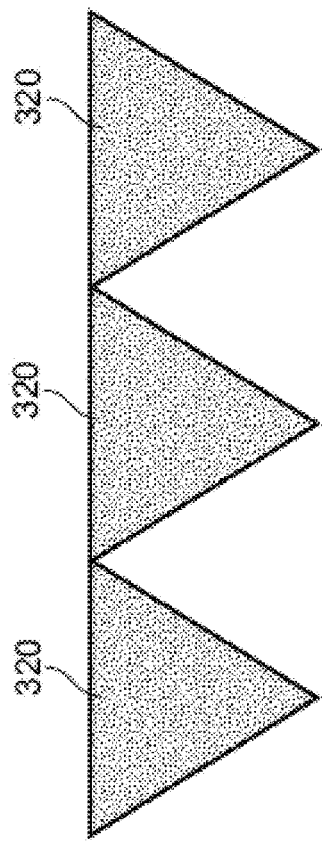
FIG. 3C is a schematic view of an isolated series of sealing members.

When taking the form of triangular patches, sealing members 320 may be individual elements, as illustrated in FIG. 3B, or a continuous series of elements, as illustrated in FIG. 3C. With sealing members 320 that are individual elements, a user may individually attach any desired number of the sealing members to corresponding portions of valve 300 in any desired pattern or location. Generally, the more sealing members 320 that are used, the greater the profile and general bulkiness of valve 300. If certain areas of valve 300 are particularly prone to PV leak, it may be desirable to strategically attach individual sealing members 320 to the valve only in those prone areas. For example, an area of valve 300 proximal to each CAF 316 may be particularly prone to PV leak. During operation, when valve 300 is closed and the pressure distal to the valve is greater than the pressure proximal to the valve, a proximally directed force may cause portions of stent 302, such as CAFs 316, to pull radially inward, exposing areas of the valve to potential PV leak. By using individual sealing members 320 only in those areas, sealing against PV leak may be maximized while minimizing the profile and/or bulkiness of valve 300.

Alternatively, sealing members 320 may take the form of a plurality of triangular patches in series. Although FIG. 3C illustrates three sealing members 320 in series, more or less may be acceptable. For example, if the first row 312a of cells 312 includes nine cells spanning the circumference of annulus section 340, it may be preferable to use nine sealing members 320 connected together as a single element. This configuration may be particularly convenient, enabling the user to handle only a single piece of material. In this configuration, sealing members 320 may be attached to cuff 306 such that, for each cell 312 in a particular row of cells, one sealing member is positioned substantially within each cell. However, this may also be achieved by attaching nine individual sealing members 320 to cuff 306, or by using a combination of individual sealing members and sealing members attached to one another in series. The term "substantially within" refers to the fact that, although each sealing member 320 is preferably positioned mostly within a particular cell 312 such that it may billow open through the cell with relatively little resistance, some minimal amount of the cell structure may overlap a portion of the sealing member.

Each sealing member 320 may be attached to cuff 306, or to both the cuff and stent body 302. Preferably, each sealing member 320 is attached only to cuff 306 and is capable of parachuting or billowing open through a cell 312 of stent body 302 upon blood entering the sealing member. By attaching sealing members 320 to cuff 306 only, rather than to both the cuff and stent body 302, the overall bulkiness and/or profile of valve 300 may be reduced.

For this and other embodiments described herein, it should also be noted that sealing members 320, when valve 300 is implanted in a patient, may be situated sub-annularly, intra-annularly, and/or supra-annularly. The particular position of sealing members 320 with respect to the native annulus may be affected by, for example, the particular position of the sealing members on stent body 302. There may be particular advantages and disadvantages of each position. For example, if the sealing members are positioned supra-annularly, they may be less likely to be distorted by the shape of the native annulus. However, this positioning may be more likely to result in coronary blockage, a larger profile in a relatively bulky area of the valve, and the positioning may be coincident with the most calcified areas of the native anatomy. If the sealing members are positioned intra-annularly, they may provide for sealing above and below the annulus without causing other physiological issues. However, this positioning may lead to interference with anchoring features of a prosthetic valve, which may lead to a higher likelihood of valve migration or a larger profile in a relatively bulky area of the valve. Finally, if the sealing members are positioned sub-annularly, the valve may have a relatively small profile and the sealing members may be coincident with the least calcified portions of the native anatomy. However, this positioning may increase the likelihood of mitral valve or conduction interference, may require a longer delivery device and may result in a decreased tracking ability of the valve.

A number of variables may be manipulated to change the way in which, and how much, each sealing member 320 billows open during retrograde blood flow. For example, the type of material forming sealing member 320 may influence how it billows open. In particular, forming sealing member 320 from a material with high compliance, such as tissue, including bovine or porcine tissue, may cause the sealing member to open to a greater extent upon retrograde blood flow in comparison to a lower compliance material. Similarly, forming sealing member 320 from a thin material may lead the sealing member to open to a greater extent upon retrograde blood flow in comparison to a thicker material. The method of attaching sealing members 320 to valve 300 may also affect how the sealing members open. For example, loosely sewing sealing members 320 to cuff 306, such that the sealing members have a relatively large amount of slack, may lead the sealing members to open to a greater extent upon retrograde blood flow in comparison to a method in which the sealing members have relatively little slack from being sewn tightly to the cuff.

Figure 3D:
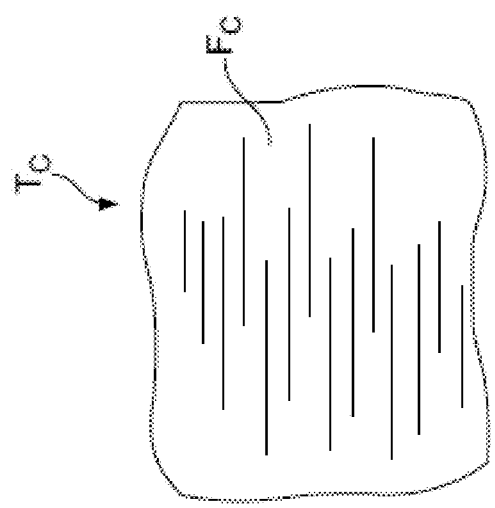
FIGS. 3D-E are enlarged views showing portions of sealing members having different fiber orientations.
Figure 3E:
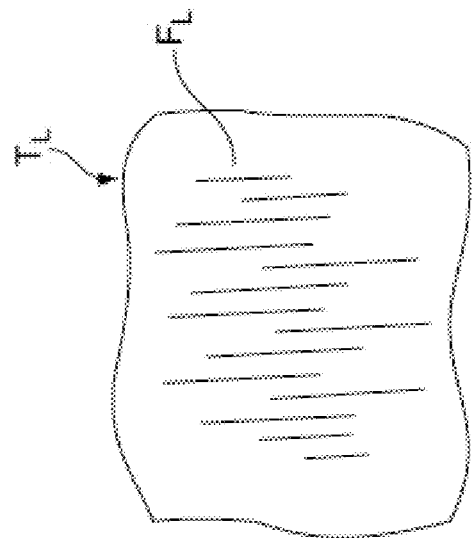

Still further, features such as orientation of fibers in the material used to form sealing members 320 may affect performance. For example, if sealing member 320 is formed from tissue and is attached to valve 300 with the fibers of the tissue oriented predominantly circumferentially, the fibers may have a spring-like effect and resist opening. This may result in relatively little billowing of sealing member 320 upon retrograde blood flow in comparison to a sealing member attached to the valve with tissue fibers oriented predominantly longitudinally. Regarding the fiber orientation, FIG. 3D illustrates tissue portion $T_c$ in which tissue fibers $F_c$ are oriented predominantly in a direction that is substantially circumferential. That is, when sealing member 320 is attached to valve 300, tissue fibers $F_c$ would predominantly align along the circumferential direction of the valve. FIG. 3E illustrates tissue portion $T_L$ in which tissue fibers $F_L$ are oriented predominantly in a direction that is substantially longitudinal, i.e., a direction that, when sealing member 320 is assembled to valve 300, is substantially parallel to the longitudinal axis of the valve. Sealing members 320 may also be formed so that the predominant fiber orientation of the tissue is between circumferential and longitudinal, and may provide for intermediate extents of billowing of the sealing members. Various methods, such as polarized light microscopy, deflection testing and/or tensioning, may be used to determine the dominant tissue fiber orientation. The above description regarding fiber orientation may also apply to other materials. For example, a sealing member made from fabric may also function differently depending on the orientation of the fibers in the fabric. However, the difference in opening of tissue with longitudinal versus circumferential fiber orientation may be exaggerated in comparison to the difference in opening of fabric with longitudinal versus circumferential fiber orientation.

Figure 3F:
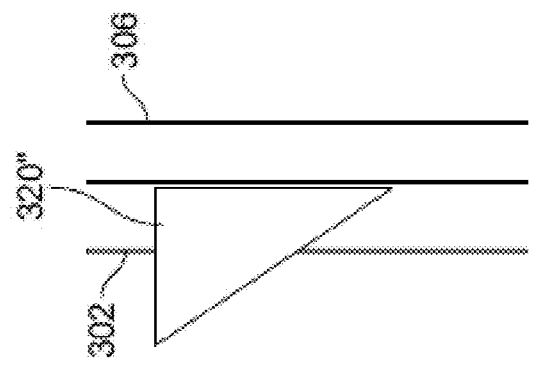
FIGS. 3F-G are highly schematic longitudinal cross-sections showing a sealing member of a valve billowing open to different extents.
Figure 3G:
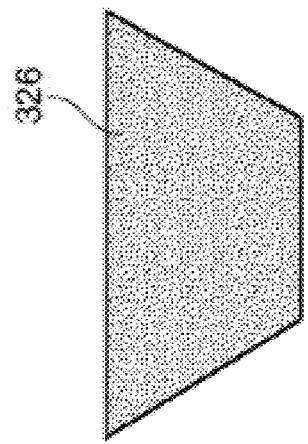

FIGS. 3F-G illustrate a schematic cross-section of a portion of valve 300 with sealing member 320' (or 320") attached to cuff 306 and billowed open through an open portion of stent body 302. In FIG. 3F, sealing member 320' may, for example, be thin, with longitudinally oriented fibers, and may be loosely sewn to cuff 306 so that the sealing member has a relatively large amount of slack. In FIG. 3G, sealing member 320" may, for example, be thick, with circumferentially oriented fibers, and may be tightly sewn to cuff 306 so that the sealing member has a relatively small amount of slack. All else being equal, a given amount of retrograde blood flow may cause sealing member 320' of FIG. 3F to billow open to a greater extent than sealing member 320" of FIG. 3G. These variables may be manipulated such that sealing member 320 opens a desired amount upon exposure to retrograde blood flow. In fact, it may be desirable to pre-shape the sealing members such that they have an open configuration, but still may be crimped along with the prosthetic valve during delivery such that, upon delivery into a final expanded configuration, the sealing member returns to an original open shape that tends to maximize the ability to capture retrograde blood flow therein.

Figure 3H:
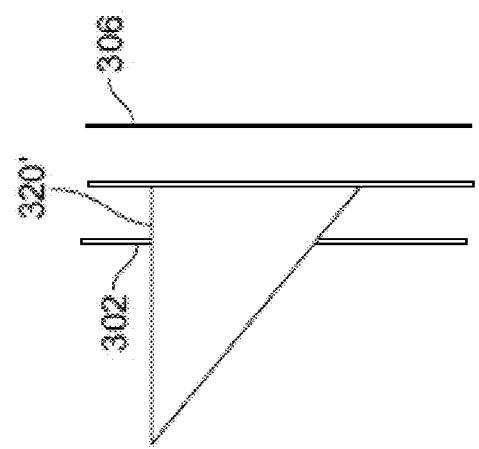
FIGS. 3H-I are schematic views of isolated individual sealing members with different shapes.
Figure 3I:
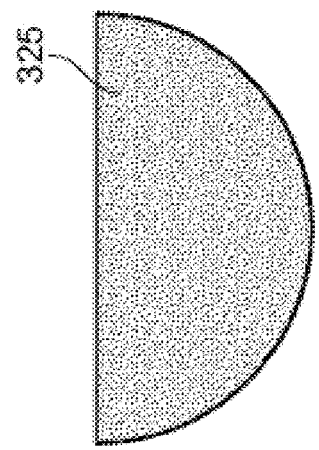

Sealing member 320 may also take shapes other than generally triangular. For example, FIG. 3H shows a sealing member 325 that has a generally semicircular shape, while FIG. 3I shows a sealing member 326 that has a generally trapezoidal shape. However, it should be understood that shapes other than those specifically disclosed herein may be suitable for use as a sealing member. Considerations that may be relevant to the suitability of such an alternate shape include the extent to which the alternate shape matches the shape of the cell 312 through which it billows open. For example, when attaching a sealing member with an alternate shape to cuff 306 and inside stent body 302, the shape preferably allows the sealing member to open through the open portion of the particular cell 312. A sealing member with a shape similar to that of the cell 312 through which it opens may be able to open relatively easily upon retrograde blood flow, while the matching shape may maximize the volume of blood capable of entering the sealing member. Further, a sealing member with a straight, curved, or otherwise non-pointed proximal side, such as the curved proximal side of sealing member 325 or the straight proximal side of sealing member 326, may provide benefits over sealing members with pointed proximal sides, such as generally triangular sealing member 320. In particular, a pointed proximal side may tend to cause blood trapped therein to stagnate, while a non-pointed proximal side may reduce the tendency for blood to stagnate, thereby reducing the likelihood of the formation of a thrombus, for example. Further, the pointed proximal side of such a sealing member may not provide an adequate volume into which blood may flow compared to a similar shape with a non-pointed proximal side.

The width of the open sides of the sealing members, such as open side 321 of sealing member 320, may also be varied. For example, the sealing members may have wider openings than those illustrated to maximize the likelihood of capturing retrograde blood flow. The wide openings, or any other sealing member openings described herein, may also alternately be punctuated by frequent stitches or other mechanisms to close portions of the open side. The effect of frequently spaced sutures, for example, may create a number of smaller openings that still allow blood flow to enter the particular sealing member. However, if a thrombus forms within the sealing member, the reduced sized openings may make it less likely that the thrombus may exit the sealing member into the blood flow.

Figure 4A:
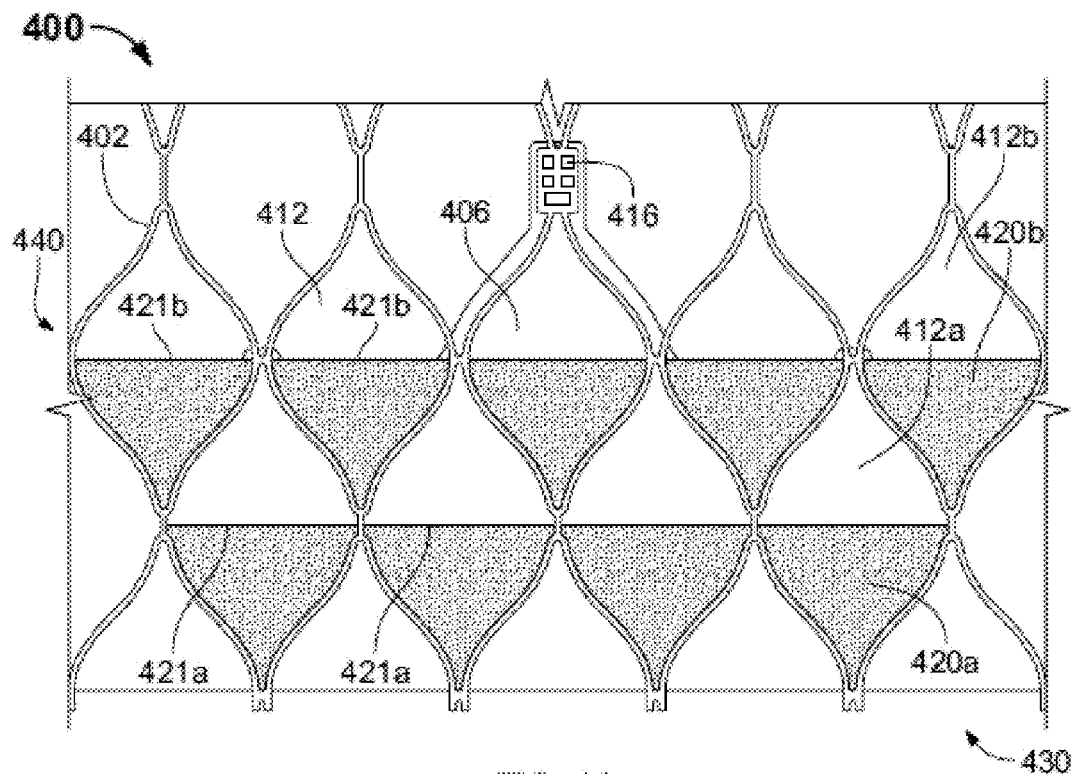
FIG. 4A is an enlarged partial schematic view of a sealing member attached to a stent according to another embodiment of the disclosure.

FIG. 4A illustrates a portion of prosthetic heart valve 400 according to another embodiment of the disclosure. Prosthetic heart valve 400 may be similar or identical to prosthetic heart valve 300 in all respects other than the active sealing mechanism. For example, prosthetic heart valve 400 includes an expandable stent 402 with a plurality of CAFs 416 (only one illustrated in FIG. 4A). Stent 402 extends from proximal or annulus end 430 to a distal or aortic end (not shown), and includes annulus section 440 adjacent the proximal end and an aortic section (not shown) adjacent the distal end. Each of the sections of stent 402 includes a plurality of cells 412 connected to one another in one or more annular rows around the stent. For example, as shown in FIG. 4A, annulus section 440 may have two annular rows of cells 412, including a first proximalmost row of cells 412a and a second row of cells 412b distal to the first row. Valve 400 may also include cuff 406, which may be substantially similar to cuff 306 of FIG. 3A. In the illustrated embodiment, cuff 406 is positioned on the luminal side of stent 402 and attached to the stent, for example, by sutures (not illustrated).

Prosthetic heart valve 400 includes sealing members 420 that provide an active sealing mechanism for sealing against PV leak. Similar to valve 300, the sealing members 420 take the form of generally triangular patches or parachute-like members that billow open when blood flows into them. However, valve 400 includes proximal sealing members 420a positioned along the first row of cells 412a as well as distal sealing members 420b positioned along the second row of cells 412b. All of the considerations discussed above with respect to sealing members 320 of FIG. 3A apply with equal force to sealing members 420a and 420b of FIG. 4A. Sealing members 420b on the second row of cells 412b may provide for additional sealing against PV leak. For example, points at which open sides 421a of two adjacent sealing members 420a meet may be less likely to catch retrograde blood flow. In the illustrated embodiment, a second row of sealing members 420b is positioned such that center portions of the open sides 421b of sealing members 420b generally align longitudinally with points at which open sides 421a of two adjacent sealing members 420a meet. In other words, the position of the center of open sides 421a of the first row of sealing members 420a is circumferentially staggered or offset from the position of the center of open sides 421b of the second row of sealing members 420b. This configuration may decrease the likelihood that retrograde blood flow will travel proximally between two adjacent sealing members 420a without being caught in any sealing member.

Figure 4B:
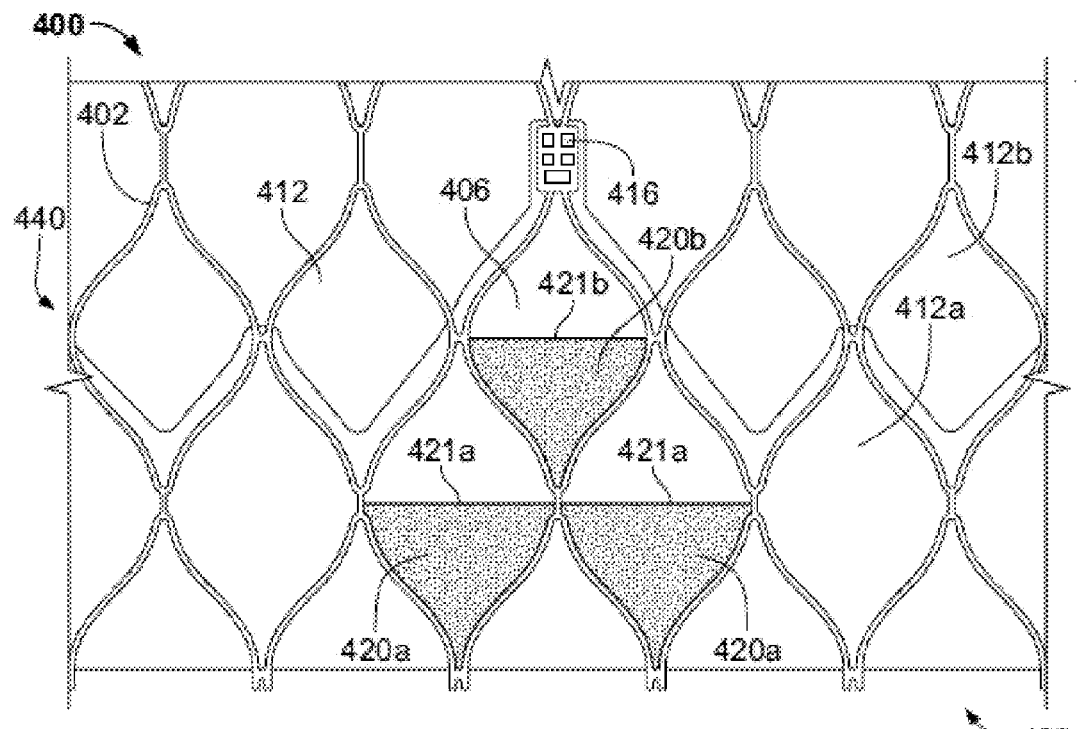
FIG. 4B is an enlarged partial schematic view of a sealing member attached to a stent according to a further embodiment of the disclosure.

As described with respect to sealing members 320, sealing members 420a, 420b may be individually attached to cuff 406, or multiple sealing members may first be connected to one another in a series for convenience. For example, in one embodiment, sealing members 420a, 420b may be attached to cuff 406 at each cell 412 in the first and second rows of cells 412a, 412b, respectively. Also as described with respect to sealing members 320, sealing members 420a, 420b may be placed strategically on valve 400 to maximize sealing against PV leak while minimizing the number of the sealing members, and therefore minimizing the bulk of the valve. One embodiment that may be particularly effective, illustrated in FIG. 4B, includes only a single sealing member 420b on the cells 412 in the second row of cells 412b that are directly proximal to each CAF 416. For each sealing member 420b on the second row of cells 412b, two sealing members 420a are positioned on the first row of cells 412a below the sealing member 420b, such that the center portion of the open side 421b of the sealing member 420b generally aligns longitudinally with the point at which the open sides 421a of the adjacent sealing members 420a meet.

Figure 4C:
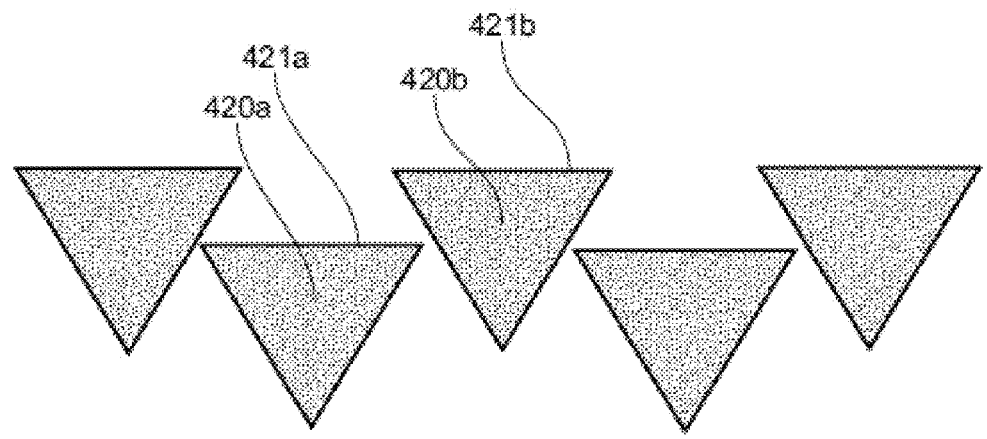
FIG. 4C is a schematic view of isolated sealing members arranged in a staggered pattern.

A number of alternate configurations of sealing members may be utilized. As described above, sealing members, such as sealing members 420a and 420b, may be positioned on the inner diameter of stent body 402, that is, between the stent body and cuff 406. However, they may alternately be placed on the outer diameter of stent body 402. If positioned on the outer diameter, more shapes and configurations may be used since the sealing members no longer need to be capable of billowing open through the open cells of stent body 402. Rather, if on the outer diameter of stent body 402, the positions of open cells of stent body 402 do not limit the shape or configuration of the sealing members at all. For example, FIG. 4C illustrates a schematic view of sealing members 420a, 420b arranged in a staggered pattern, with the remainder of prosthetic valve 400 not illustrated. In this configuration, a first row of sealing members 420a is positioned in a staggered relationship with a second row of sealing members 420b. Open sides 421a of sealing members 420a are positioned proximally relative to open sides 421b of sealing members 420b. However, there is some overlap between sealing members 420a, 420b. In particular, open sides 421a of sealing members 420a are positioned approximately at a midline of sealing members 420b. In other words, the proximal-to-distal distance between open sides 421b and 421a is approximately equal to the proximal-to-distal distance between open sides 421a of sealing members 420a and the proximalmost points of sealing members 420b. These distances may be varied, however, to increase or decrease the level of staggering and overlap between sealing members 420a and 420b. It should further be noted that, in this particular embodiment, it may be preferable for sealing members 420a, 420b to be attached to the outer diameter of stent body 402, rather than between the stent body 402 and cuff 406. This may be preferable if the shape and position of sealing members 420a, 420b does not match with the shape and position of the open cells of stent body 402 such that the sealing members may easily billow open through the open cells. By staggering sealing members 420a, 420b, the profile of valve 400 may be reduced in comparison to a configuration in which sealing members 420a, 420b are aligned in a single non-staggered row. Still further, it should be noted that in the embodiments described herein, one row, two rows, or more rows of sealing members may be suitable for use with a prosthetic heart valve.

Figure 5:
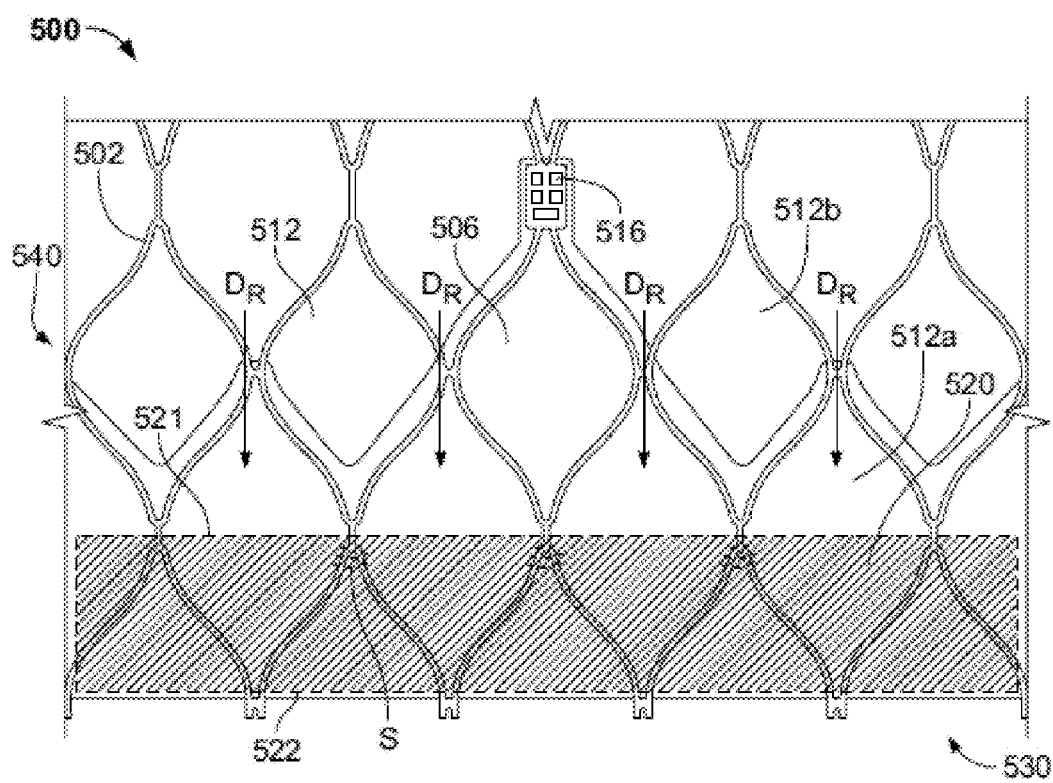
FIG. 5 is an enlarged partial schematic view of a sealing member attached to a stent according to still another embodiment of the disclosure.

FIG. 5 illustrates a portion of prosthetic heart valve 500 according to a further embodiment of the disclosure. Prosthetic heart valve 500 may be similar or identical to prosthetic heart valves 300 and 400 in all respects other than the active sealing mechanism. For example, prosthetic heart valve 500 includes an expandable stent 502 with a plurality of CAFs 516 (only one illustrated in FIG. 5). Stent 502 extends from proximal or annulus end 530 to a distal or aortic end (not shown), and includes annulus section 540 adjacent the proximal end and an aortic section (not shown) adjacent the distal end. Each of the sections of stent 502 includes a plurality of cells 512 connected to one another in one or more annular rows around the stent. For example, as shown in FIG. 5, annulus section 540 may have two annular rows of cells 512, including a first proximalmost row of cells 512a and a second row of cells 512b distal to the first row. Valve 500 may also include a cuff 506, which may be substantially similar to cuffs 306 and 406 of FIGS. 3A and 4A, respectively. In the illustrated embodiment, cuff 506 is positioned on the luminal side of stent 502 and attached to the stent, for example, by sutures (not illustrated).

Prosthetic heart valve 500 includes a sealing member 520 that provides an active sealing mechanism for sealing against PV leak. Sealing member 520 may take the form a rectangular patch that functions as a parachute-like member that billows open when blood flows into it. In the illustrated embodiment, sealing member 520 includes an open distal side 521 and a closed proximal side 522. The proximal side 522 of sealing member 520 may be attached, for example by sewing, to cuff 506. The attachment is preferably such that blood entering sealing member 520 cannot exit through the closed proximal side 522 of the sealing member. In this configuration, sealing member 520 defines a pocket. The pocket may include regions defined by the points at which sealing member 520 near the open side 521 is attached to cuff 506, as described below. Each region of the pocket may be in fluid communication with adjacent regions. The rectangular patch may be wrapped around the entire circumference of stent 502 with ends of the patch attached to one another to secure the patch in a desired position. In this embodiment, sealing member 520 is a separate entity from cuff 506. Further, in this embodiment, sealing member 520 is preferably attached over the outside of both cuff 506 and stent 502 to allow the sealing member to billow open. This is in contrast to other embodiments, such as generally triangular sealing members 320, which preferably are attached between cuff 306 and stent 302 and which are capable of billowing open through cells 312 of the stent.

One or more individual rectangular patches may be individually attached to stent 502 such that the collective patches are wrapped partially, or entirely, around the circumference of the stent. Portions of sealing member 520 near the open side 521 are also preferably attached to cuff 506, for example using sutures S. As illustrated, a small number of stitches, such as two or three, connect distal portions of sealing member 520 to cuff 506 at spaced locations around the circumference of the sealing member. While the sutures S are shown as attaching sealing member 520 to cuff 506 along portions of the struts where adjacent cells 512a meet, the connections may be made at any point on the cuff. The distal attachments preferably are few enough to leave a substantial portion of open side 521 free such that retrograde blood flow may freely flow into sealing member 520, while still providing enough support to maintain the position of the distal end of the sealing member relative to cuff 506. Similar to embodiments described above, if blood flows in the retrograde direction, represented by arrows $D_R$, on the abluminal side of the valve 500, the blood may flow into sealing member 520 between the points at which the sealing member is attached to cuff 506. The blood may enter and fill sealing member 520, causing it to expand similar to an inner tube, facilitating the creation of a seal against PV leak between valve 500 and the native tissue in which the valve is positioned.

Sealing member 520 may alternately be formed as an extension of cuff 506, rather than one or more separate rectangular patches. For example, cuff 506, which is positioned on the luminal side of valve 500, may include a portion which extends beyond the proximal end of stent 502. This extending portion may be folded or wrapped around the proximal end of stent 502 such that the extending portion is on the abluminal side of valve 500. The extending portion would form sealing member 520 and would otherwise act similarly to separate rectangular patches attached to cuff 506. In this embodiment, in which sealing member 520 is an extension of cuff 506, it may not be necessary to suture or otherwise attach the proximal end of the sealing member to the cuff, since the sealing member is an extension of the cuff. However, it still may be preferable to form a seam, for example with a suture, between sealing member 520 and cuff 506 adjacent the proximal ends thereof. This may, for example, provide structural support to sealing member 520.

Figure 6A:
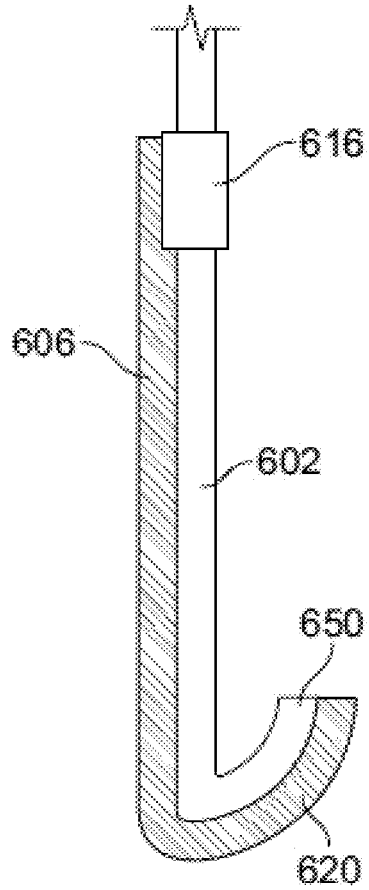
FIG. 6A is a highly schematic partial longitudinal cross-section of a sealing member attached to a stent, with the stent in an expanded configuration, according to yet another embodiment of the disclosure.
Figure 6B:
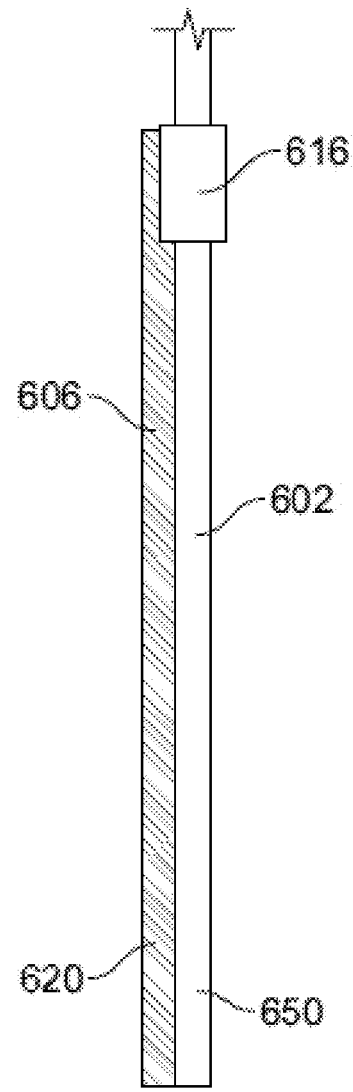
FIG. 6B is a highly schematic partial longitudinal cross-section of the sealing member and stent of FIG. 6A in a collapsed configuration.

FIG. 6A illustrates a sealing member 620 according to another embodiment of the disclosure. FIG. 6A is a highly schematic sectional view of a proximal portion of a stent body 602 for use in a prosthetic heart valve. As illustrated, a strut of stent body 602 extends proximally from CAF 616 to a proximal end of the stent, at which point the strut transitions into a finger 650 that curves radially outwardly and distally in a general "J" shape. In other words, the strut forms finger 650 at a proximal end of the strut. Cuff 606 may be attached on the luminal side of stent 602 and extend toward the proximal end of the stent, and then curve back up radially outwardly and distally, following the contour of finger 650. In this embodiment, cuff 606 may extend partially or completely around the circumference of stent 602, attached to a discrete number of fingers 650. This embodiment functions similarly to the embodiment described above in which sealing member 520 forms an extension of cuff 506 that is folded or wrapped over the proximal end of stent 502. However, the use of fingers 650 may be beneficial, as the arms may be set to curve outwardly only after stent 602 is deployed and transitions from a collapsed condition to an expanded condition. For example, FIG. 6B illustrates stent 602 and finger 650, along with cuff 606 and sealing member 620, prior to deployment when it is in a collapsed condition, for example within a delivery device. In this configuration, finger 650 lies substantially flat with respect to stent body 602. This configuration allows for the collapsed profile to remain relatively small, since finger 650 and sealing member 620 do not curve outwardly until stent 602 is released from a delivery device and transitions into the expanded condition illustrated in FIG. 6A. Once in the expanded condition, retrograde blood flowing into the sealing member 620 may cause the sealing member to expand further or fill up like an inner tube, helping to create a seal between the valve and the native tissue in which the valve is implanted.

Figure 7:
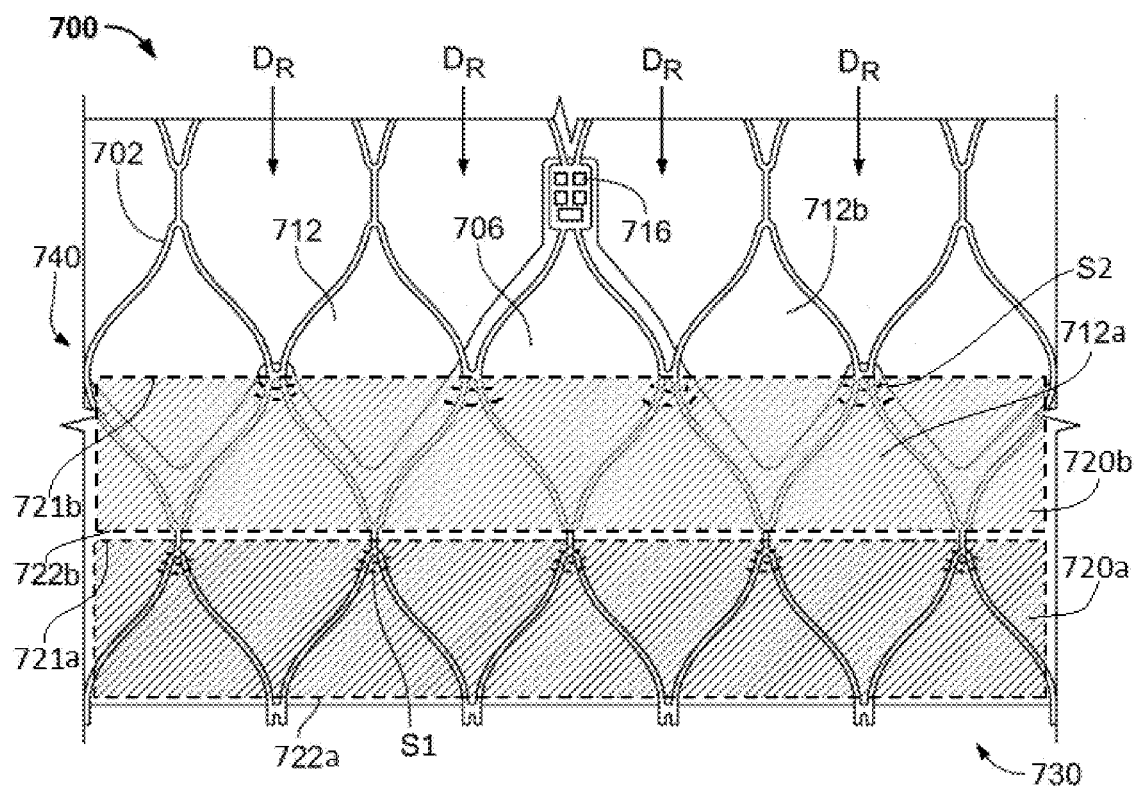
FIG. 7 is an enlarged partial schematic view of two sealing members attached to a stent according to yet a further embodiment of the disclosure.

FIG. 7 illustrates a portion of prosthetic heart valve 700 according to a further embodiment of the disclosure. Prosthetic heart valve 700 may be similar or identical to prosthetic heart valve 500 in most respects. For example, prosthetic heart valve 700 includes an expandable stent 702 with a plurality of CAFs 716 (only one illustrated in FIG. 7). Stent 702 extends from a proximal or annulus end 730 to a distal or aortic end (not shown), and includes annulus section 740 adjacent the proximal end and an aortic section (not shown) adjacent the distal end. It should be understood that, when implanted in a native aortic or pulmonary valve, the proximal end may be referred to as the inflow or inlet end, and the distal end may be referred to as the outflow or outlet end. It should further be understood that, if placed in a native atrioventricular valve such as the mitral valve, a proximal end of the stent may be referred to as an outflow end.

Each of the sections of stent 702 includes a plurality of cells 712 connected to one another in one or more annular rows around the stent. For example, as shown in FIG. 7, annulus section 740 may have two annular rows of cells 712, including a first proximalmost row of cells 712a and a second row of cells 712b distal to the first row. Valve 700 may also include a cuff 706, which may be substantially similar to cuff 506 of FIG. 5. In the illustrated embodiment, cuff 706 is positioned on the luminal side of stent 702 and attached to the stent, for example, by sutures (not illustrated).

Prosthetic heart valve 700 includes sealing members 720a, 720b that provide an active sealing mechanism for sealing against PV leak. Sealing members 720a and 720b may each take a similar or identical form as sealing member 520 of prosthetic heart valve 500. For example, sealing member 720a may be a rectangular patch that functions as a parachute-like member that billows open when blood flows into it. In the illustrated embodiment, sealing member 720a includes an open distal side 721a and a closed proximal side 722a. The proximal side 722a of sealing member 720a may be attached, for example by sewing, to cuff 706. The attachment is preferably such that blood entering sealing member 720a cannot exit through the closed proximal side 722a of the sealing member. In this configuration, sealing member 720a defines a pocket. The pocket may include regions defined by the points at which sealing member 720a near the open side 721a is attached to cuff 706, as described below. Each region of the pocket may be in fluid communication with adjacent regions. The rectangular patch may be wrapped around the entire circumference of stent 702 with ends of the patch attached to one another to secure the patch in a desired position. In this embodiment, sealing member 720a is a separate entity from cuff 706. Further, in this embodiment, sealing member 720a is preferably attached over the outside of both cuff 706 and stent 702 to allow the sealing member to billow open.

Sealing member 720a may take the form of a single rectangular patch, or multiple patches connected to one another to form a rectangular patch that is long enough to extend around the entire circumference of annulus portion 740. Portions of sealing member 720a near the open side 721a are also preferably attached to cuff 706, for example using sutures S1. As illustrated, a small number of stitches, such as two or three, connect distal portions of sealing member 720a to cuff 706 at spaced locations around the circumference of the sealing member. In particular, the sutures S1 may be placed near where one cell 712a meets a circumferentially adjacent cell 712a, so that the pocket formed in sealing member 720a has a plurality of openings, each of which having a width substantially equal to a maximum circumferential width of a cell 712a when stent 702 is in the expanded condition. While the sutures S1 are shown as attaching sealing member 720a to cuff 706 along portions of the struts where adjacent cells 712a meet, the connections may alternatively be made at any point on the cuff. The distal attachments preferably are few enough to leave a substantial portion of open side 721a free such that retrograde blood flow may freely flow into sealing member 720a, while still providing enough support to maintain the position of the distal end of the sealing member relative to cuff 706.

Valve 700 may include a second sealing member 720b, which may take the form of a rectangular patch similar or identical to sealing member 720a (or similar to any described alternative way to form sealing member 720a). Sealing member 720b may be positioned mostly or entirely distal to sealing member 720a, so that a closed proximal side 722b of sealing member 720b is positioned adjacent to or spaced apart from the open distal side 721a of sealing member 720a. Closed proximal side 722b may be attached to cuff 706 with sutures or any other suitable fastening mechanism so that blood entering sealing member 720b from the open side 721b is unable to exit sealing member 720b through the closed side 722b. Similar to sealing member 720a, the open side 721b of sealing member 720b may be coupled to cuff 706 and/or struts of stent 702 at circumferentially spaced apart locations to form a plurality of openings leading into the pocket of sealing member 720b. In the illustrated embodiment, sutures S2 attach portions of the distal side of sealing member 720b at locations of cuff 706 and/or stent 702 at which a cell 712b in the second circumferential row meets a circumferentially adjacent cell 712b in that same row. With this configuration, the openings in open side 721b of sealing member 720b generally correspond to the maximum width of a cell 712b in the expanded condition of stent 702. This allows for circumferential positional staggering of the openings in the open side 721b of sealing member 720b compared to the openings in the open side 721a of sealing member 720a.

Similar to embodiments described above, if blood flows in the retrograde direction, represented by arrows $D_R$, on the abluminal side of valve 700, the blood may flow into sealing member 720a between the points at which the sealing member is attached to cuff 706. The blood may enter and fill sealing member 720, causing it to expand similar to an inner tube, facilitating the creation of a seal against PV leak between valve 700 and the native tissue in which the valve is positioned. To the extent that retrograde blood flow is less likely to enter sealing member 720a at the positions at which open side 721a is sutured to the cuff 706 and/or stent 702, such retrograde blood flow may be likely to enter sealing member 720b since the corresponding locations of open side 721b of sealing member 720b will be free to open and receive retrograde blood flow. In other words, the use of two sealing members 720a-b with the attachment locations described above may provide for similar additional capability of mitigating PV leak as described in connection with the circumferentially staggered patches 421a-b of FIG. 4A.

Similar to sealing member 520, first sealing member 720a may alternately be formed as an extension of cuff 706, with cuff 706 including a portion which extends beyond the inflow edge of stent 702. This extending portion may be folded or wrapped around the inflow edge of stent 702 such that the extending portion is on the abluminal side of valve 700. The extending portion would form first sealing member 720 and would otherwise act similarly to a rectangular patch attached to cuff 706. In this embodiment, in which first sealing member 720a is an extension of cuff 706, it may not be necessary to suture or otherwise attach the proximal end of the first sealing member 720a to the cuff 706, since the sealing member is an extension of the cuff. However, it still may be preferable to form a seam, for example with a suture, between first sealing member 720a and cuff 706 adjacent the proximal ends thereof. This may, for example, provide structural support to first sealing member 720a.

Still further, first sealing member 720a and/or second sealing member 720b may be configured to wrap around only a part of the circumference of stent 702. This may allow, for example, strategic placement of sealing members 720a and/or 720b to maximize the likelihood of the sealing members 720a and/or 720b receiving retrograde blood flow while minimizing the amount of material and bulk added to valve 700. In one example of this, similar to the embodiment described in connection with FIG. 4B, second sealing member 720b may extend partially around the circumference of stent 702 proximal to the CAFs 716, with first sealing member 720a extending partially around the circumference of stent 702 proximal to CAFs 716 and proximal to second sealing member 720b. In this embodiment, first sealing member 720a and second sealing member 720b may each comprise a plurality of individual patches, such as rectangular patches, positioned to catch retrograde blood flow on the abluminal side of stent 702 near the CAFs, which area may be particularly susceptible to PV leak, as described above in connection with FIG. 4B. It should be understood if some other portion of valve 700 is determined to be particularly susceptible to PV leak, the sealing members 720a and/or 720b may be positioned at those locations to increase the likelihood of mitigating such PV leak.

According to one aspect of the disclosure, a prosthetic heart valve comprises:

a collapsible and expandable stent body including a generally tubular annulus section;

one or more prosthetic valve elements mounted to the stent body and operative to allow flow in an antegrade direction but to substantially block flow in a retrograde direction through the annulus section;

a cuff attached to the stent body;

a first sealing member attached to the cuff, the first sealing member extending circumferentially around an abluminal surface of the stent body and having an open side facing in a first axial direction and a closed side facing in a second axial direction opposite to the first axial direction so that a flow of blood in the second axial direction will tend to force blood into the first sealing member and cause the first sealing member to billow outwardly relative to the stent body; and a second sealing member attached to the cuff, the second sealing member extending circumferentially around the abluminal surface of the stent body and having an open side facing in the first axial direction and a closed side facing in the second axial direction so that the flow of blood in the second axial direction will tend to force blood into the second sealing member and cause the second sealing member to billow outwardly relative to the stent body; and/or the first sealing member defines a first pocket having a plurality of first regions, each of the first regions being in fluid communication with adjacent ones of the first regions; and/or the second sealing member defines a second pocket having a plurality of second regions, each of the second regions being in fluid communication with adjacent ones of the second regions; and/or the first sealing member is wrapped around an entire circumference of the stent body; and/or the second sealing member is wrapped around the entire circumference of the stent body; and/or the open side of the first sealing member is attached to the cuff at spaced locations around a circumference of the stent body; and/or the open side of the second sealing member is attached to the cuff at spaced locations around the circumference of the stent body; and/or the open side of the first sealing member includes a first plurality of openings and the open side of the second sealing members includes a second plurality of openings, the first plurality of openings being offset in a circumferential direction from the second plurality of openings; and/or the first sealing member is positioned nearer an inflow end of the stent body than the second sealing member; and/or the open side of the first sealing member is axially spaced apart from the closed side of the second sealing member; and/or the first sealing member comprises an extension of the cuff, the extension being wrapped around an inflow end of the stent body such that the extension is positioned on an abluminal surface of the stent body; and/or a proximal portion of the extension on the abluminal surface of the stent body is connected to a proximal portion of the cuff on the luminal surface of the stent body with a seam; and/or the second sealing member is formed from a separate piece of material from the cuff; and/or the first sealing member is formed from a separate piece of material from the cuff; and/or the first sealing member is formed of a single piece of material; and/or the second sealing member is formed of a single piece of material; and/or the first sealing member is formed from a plurality of pieces of material; and/or the second sealing member is formed from a plurality of pieces of material; and/or the first sealing member is substantially rectangular; and/or the second sealing member is substantially rectangular.

Although the prosthetic valves herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a collapsible and expandable stent body including a generally tubular annulus section;
one or more prosthetic valve elements mounted to the stent body and operative to allow flow in an antegrade direction but to substantially block flow in a retrograde direction through the annulus section;
a cuff attached to the stent body;
a first sealing member attached to the cuff, the first sealing member extending circumferentially around an abluminal surface of the stent body and having an open side facing in a first axial direction and a closed side facing in a second axial direction opposite to the first axial direction so that a flow of blood in the second axial direction will tend to force blood into the first sealing member and cause the first sealing member to billow outwardly relative to the stent body; and
a second sealing member attached to the cuff, the second sealing member extending circumferentially around the abluminal surface of the stent body and having an open side facing in the first axial direction and a closed side facing in the second axial direction so that the flow of blood in the second axial direction will tend to force blood into the second sealing member and cause the second sealing member to billow outwardly relative to the stent body, wherein the open sides of the first sealing member and the second sealing member are attached to the cuff at spaced locations around a circumference of the stent body so that the open side of the first sealing member includes a first plurality of openings offset in a circumferential direction from a second plurality of openings in the open side of the second sealing member.

2. The prosthetic heart valve of claim 1, wherein the first sealing member defines a first pocket having a plurality of first regions, each of the first regions being in fluid communication with adjacent ones of the first regions.

3. The prosthetic heart valve of claim 2, wherein the second sealing member defines a second pocket having a plurality of second regions, each of the second regions being in fluid communication with adjacent ones of the second regions.

4. The prosthetic heart valve of claim 1, wherein the first sealing member is wrapped around an entire circumference of the stent body.

5. The prosthetic heart valve of claim 4, wherein the second sealing member is wrapped around the entire circumference of the stent body.

6. The prosthetic heart valve of claim 1, wherein the first sealing member is positioned nearer an inflow end of the stent body than the second sealing member.

7. The prosthetic heart valve of claim 6, wherein the open side of the first sealing member is axially spaced apart from the closed side of the second sealing member.

8. The prosthetic heart valve of claim 1, wherein the first sealing member comprises an extension of the cuff, the extension being wrapped around an inflow end of the stent body such that the extension is positioned on an abluminal surface of the stent body.

9. The prosthetic heart valve of claim 8, wherein a proximal portion of the extension on the abluminal surface of the stent body is connected to a proximal portion of the cuff on the luminal surface of the stent body with a seam.

10. The prosthetic heart valve of claim 1, wherein the second sealing member is formed from a separate piece of material from the cuff.

11. The prosthetic heart valve of claim 10, wherein the first sealing member is formed from a separate piece of material from the cuff.

12. The prosthetic heart valve of claim 1, wherein the first sealing member is formed of a single piece of material.

13. The prosthetic heart valve of claim 1, wherein the second sealing member is formed of a single piece of material.

14. The prosthetic heart valve of claim 1, wherein the first sealing member is formed from a plurality of pieces of material.

15. The prosthetic heart valve of claim 1, wherein the second sealing member is formed from a plurality of pieces of material.

16. The prosthetic heart valve of claim 1, wherein the first sealing member is substantially rectangular.

17. The prosthetic heart valve of claim 16, wherein the second sealing member is substantially rectangular.

* * * * *